(12) United States Patent
Deck et al.

(10) Patent No.: US 9,839,419 B2
(45) Date of Patent: Dec. 12, 2017

(54) SUTURING INSTRUMENT WITH JAW HAVING INTEGRAL CARTRIDGE COMPONENT

(71) Applicant: Ethicon Endo-Surgery, LLC, Guaynabo, PR (US)

(72) Inventors: Andrew C. Deck, Dayton, OH (US); William J. White, West Chester, OH (US); Daniel J. Mumaw, Liberty Township, OH (US); David T. Martin, Milford, OH (US); Daniel L. Geiger, Ft. Thomas, KY (US); Christopher J. Hess, Cincinnati, OH (US); Michael D. Cronin, Cincinnati, OH (US); James G. Lee, Cincinnati, OH (US); Frederick E. Shelton, IV, Hillsboro, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 225 days.

(21) Appl. No.: 14/740,762

(22) Filed: Jun. 16, 2015

(65) Prior Publication Data
US 2016/0367238 A1    Dec. 22, 2016

(51) Int. Cl.
*A61B 17/04* (2006.01)
*A61B 17/00* (2006.01)

(52) U.S. Cl.
CPC .. *A61B 17/0469* (2013.01); *A61B 2017/0046* (2013.01); *A61B 2017/00398* (2013.01);
(Continued)

(58) Field of Classification Search
CPC .......... A61B 17/00234; A61B 17/0469; A61B 17/0482; A61B 17/062; A61B 17/0625;
(Continued)

(56) References Cited

U.S. PATENT DOCUMENTS

| 4,027,608 A | * | 6/1977 | Arbuckle | ............... | D05B 81/00 |
|             |   |        |          |                 | 112/169 |
| 4,557,265 A | * | 12/1985 | Andersson | ......... | A61B 17/0491 |
|             |   |        |           |          | 112/222 |

(Continued)

FOREIGN PATENT DOCUMENTS

EP    2 055 243 A2    5/2009
WO    WO 2013/158622 A1    10/2013

OTHER PUBLICATIONS

International Search Report and Written Opinion dated Nov. 14, 2016 for Application No. PCT/US2016/037348, 16 pgs.

(Continued)

*Primary Examiner* — Ryan J Severson
(74) *Attorney, Agent, or Firm* — Forst Brown Todd LLC

(57) ABSTRACT

A surgical instrument includes a body, first and second drive elements, a shaft, and a needle applier. The first drive element has a distal portion located at a distal end of the body. The second drive element has a proximal portion located at a proximal end of the shaft. The proximal portion of the second drive element is configured to removably couple with the distal portion of first drive element such that the first and second drive elements are aligned along a common axis and such that the first drive element is configured to communicate motion to the second drive element. The needle applier includes a needle and a drive assembly, which is configured to drive the needle along an orbital path about a rotation axis that is transverse to the longitudinal axis, in response to motion of the second drive element.

19 Claims, 39 Drawing Sheets

(52) U.S. Cl.
CPC ........... *A61B 2017/00473* (2013.01); *A61B 2017/00477* (2013.01); *A61B 2017/00734* (2013.01)

(58) Field of Classification Search
CPC .. A61B 2017/0023; A61B 2017/00314; A61B 2017/00349; A61B 2017/0046; A61B 2017/00473; A61B 2017/00479; A61B 2017/0608; A61B 2017/0479
See application file for complete search history.

(56) References Cited

U.S. PATENT DOCUMENTS

| | | | | |
|---|---|---|---|---|
| 4,899,746 A * | 2/1990 | Brunk | A61B 17/0491 | 112/169 |
| 5,709,693 A * | 1/1998 | Taylor | A61B 17/0491 | 606/139 |
| 5,766,186 A * | 6/1998 | Faraz | A61B 17/0469 | 606/145 |
| 5,911,727 A * | 6/1999 | Taylor | A61B 17/0491 | 606/139 |
| 6,443,962 B1 * | 9/2002 | Gaber | A61B 17/0491 | 112/80.04 |
| 7,004,951 B2 * | 2/2006 | Gibbens, III | A61B 17/0482 | 606/144 |
| 7,338,504 B2 * | 3/2008 | Gibbens | A61B 17/0482 | 606/144 |
| 7,628,796 B2 * | 12/2009 | Shelton, IV | A61B 1/00087 | 606/139 |
| 7,828,812 B2 * | 11/2010 | Stokes | A61B 1/00087 | 606/139 |
| 7,833,236 B2 * | 11/2010 | Stokes | A61B 1/00087 | 606/139 |
| 7,862,572 B2 * | 1/2011 | Meade | A61B 17/0482 | 606/145 |
| 7,887,554 B2 * | 2/2011 | Stokes | A61B 1/00087 | 606/139 |
| 7,976,553 B2 * | 7/2011 | Shelton, IV | A61B 1/00087 | 606/139 |
| 8,123,764 B2 * | 2/2012 | Meade | A61B 17/0469 | 606/139 |
| 8,474,522 B2 * | 7/2013 | Lynde | E21B 21/002 | 166/99 |
| 8,500,756 B2 * | 8/2013 | Papa | A61B 1/00087 | 606/139 |
| 8,641,728 B2 * | 2/2014 | Stokes | A61B 1/00087 | 606/139 |
| 8,702,732 B2 | 4/2014 | Woodard et al. | | |
| 8,821,519 B2 * | 9/2014 | Meade | A61B 17/0469 | 606/139 |
| 8,906,043 B2 * | 12/2014 | Woodard, Jr. | A61B 17/0469 | 606/147 |
| 9,113,861 B2 * | 8/2015 | Martin | A61B 17/062 | |
| 9,125,645 B1 * | 9/2015 | Martin | A61B 17/0469 | |
| 9,168,037 B2 | 10/2015 | Woodard et al. | | |
| 9,247,938 B2 * | 2/2016 | Martin | A61B 17/062 | |
| 9,277,916 B2 * | 3/2016 | Martin | A61B 17/0469 | |
| 9,357,998 B2 * | 6/2016 | Martin | A61B 17/0483 | |
| 9,375,212 B2 * | 6/2016 | Martin | A61B 17/0482 | |
| 9,427,226 B2 * | 8/2016 | Martin | A61B 17/0469 | |
| 9,451,946 B2 * | 9/2016 | Woodard, Jr. | A61B 17/0469 | |
| 2003/0083674 A1 * | 5/2003 | Gibbens, III | A61B 17/0482 | 606/144 |
| 2006/0069396 A1 * | 3/2006 | Meade | A61B 17/0482 | 606/144 |
| 2006/0111732 A1 * | 5/2006 | Gibbens | A61B 17/0482 | 606/145 |
| 2006/0281970 A1 * | 12/2006 | Stokes | A61B 1/00087 | 600/104 |
| 2006/0282090 A1 * | 12/2006 | Stokes | A61B 1/00087 | 606/144 |
| 2006/0282091 A1 * | 12/2006 | Shelton, IV | A61B 1/00087 | 606/144 |
| 2006/0282092 A1 * | 12/2006 | Stokes | A61B 1/00087 | 606/144 |
| 2006/0282093 A1 * | 12/2006 | Shelton, IV | A61B 1/00087 | 606/144 |
| 2006/0282094 A1 * | 12/2006 | Stokes | A61B 1/00087 | 606/144 |
| 2006/0282095 A1 * | 12/2006 | Stokes | A61B 1/00087 | 606/144 |
| 2006/0282096 A1 * | 12/2006 | Papa | A61B 1/00087 | 606/144 |
| 2006/0282098 A1 * | 12/2006 | Shelton, IV | A61B 1/00087 | 606/144 |
| 2006/0282099 A1 * | 12/2006 | Stokes | A61B 1/00087 | 606/148 |
| 2007/0239176 A1 * | 10/2007 | Stokes | A61B 17/00234 | 606/144 |
| 2007/0239177 A1 * | 10/2007 | Stokes | A61B 17/0469 | 606/144 |
| 2008/0071296 A1 * | 3/2008 | Klundt | A61B 17/0469 | 606/144 |
| 2008/0255590 A1 * | 10/2008 | Meade | A61B 17/0482 | 606/144 |
| 2009/0108048 A1 * | 4/2009 | Zemlok | A61B 17/07207 | 227/175.1 |
| 2009/0209980 A1 | 8/2009 | Harris | | |
| 2010/0152751 A1 * | 6/2010 | Meade | A61B 17/0469 | 606/144 |
| 2011/0278344 A1 * | 11/2011 | Zemlok | A61B 17/07207 | 227/176.1 |
| 2012/0130404 A1 * | 5/2012 | Meade | A61B 17/0469 | 606/145 |
| 2012/0143223 A1 * | 6/2012 | Woodard, Jr. | A61B 17/0469 | 606/147 |
| 2012/0220989 A1 * | 8/2012 | Zemlok | A61B 17/07207 | 606/1 |
| 2012/0289975 A1 * | 11/2012 | Martin | A61B 17/062 | 606/147 |
| 2012/0290005 A1 * | 11/2012 | Martin | A61B 17/062 | 606/232 |
| 2013/0245647 A1 * | 9/2013 | Martin | A61B 17/0469 | 606/147 |
| 2013/0245648 A1 * | 9/2013 | Martin | A61B 17/0469 | 606/147 |
| 2013/0282027 A1 * | 10/2013 | Woodard, Jr. | A61B 17/0469 | 606/144 |
| 2013/0282031 A1 * | 10/2013 | Woodard, Jr. | A61B 17/062 | 606/147 |
| 2014/0171970 A1 | 6/2014 | Martin et al. | | |
| 2014/0305988 A1 * | 10/2014 | Boudreaux | A61B 17/068 | 227/175.3 |
| 2015/0090764 A1 * | 4/2015 | Zemlok | A61B 17/07207 | 227/176.1 |
| 2015/0127024 A1 | 5/2015 | Berry | | |
| 2015/0133967 A1 | 5/2015 | Martin | | |
| 2015/0142020 A1 * | 5/2015 | Woodard, Jr. | A61B 17/0469 | 606/147 |
| 2015/0327857 A1 * | 11/2015 | Zemlok | A61B 17/07207 | 227/176.1 |
| 2015/0351748 A1 * | 12/2015 | White | A61B 17/0482 | 606/145 |
| 2016/0120740 A1 * | 5/2016 | Rawls-Meehan | A61H 23/0263 | 601/49 |
| 2016/0367238 A1 * | 12/2016 | Deck | A61B 17/0469 | |
| 2016/0367243 A1 | 12/2016 | Martin et al. | | |

OTHER PUBLICATIONS

U.S. Appl. No. 14/297,993, filed Jun. 6, 2014.
U.S. Appl. No. 14/298,038, filed Jan. 30, 2015.

* cited by examiner

SUTURING INSTRUMENT WITH JAW HAVING INTEGRAL CARTRIDGE COMPONENT

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure.

Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laproscopic Suture Device with Asynchronous In-Line Needle Movement," published Dec. 22, 2011, now U.S. Pat. No. 9,168,037, issued on Oct. 27, 2015, the disclosure of which is incorporated by reference herein; U.S. Pub. No. 2014/0171970, entitled "Circular Needle Applier with Articulating and Rotating Shaft," published Jun. 19, 2014, now U.S. Pat. No. 9,357,998, issued on Jun. 7, 2016, the disclosure of which is incorporated by reference herein; and U.S. patent application Ser. No. 14/297,993, entitled "Jawed Cartridge receiving assembly for Needle Cartridge," filed Jun. 6, 2014, published as U.S. Pub. No. 2016/0046096 on Feb. 18, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
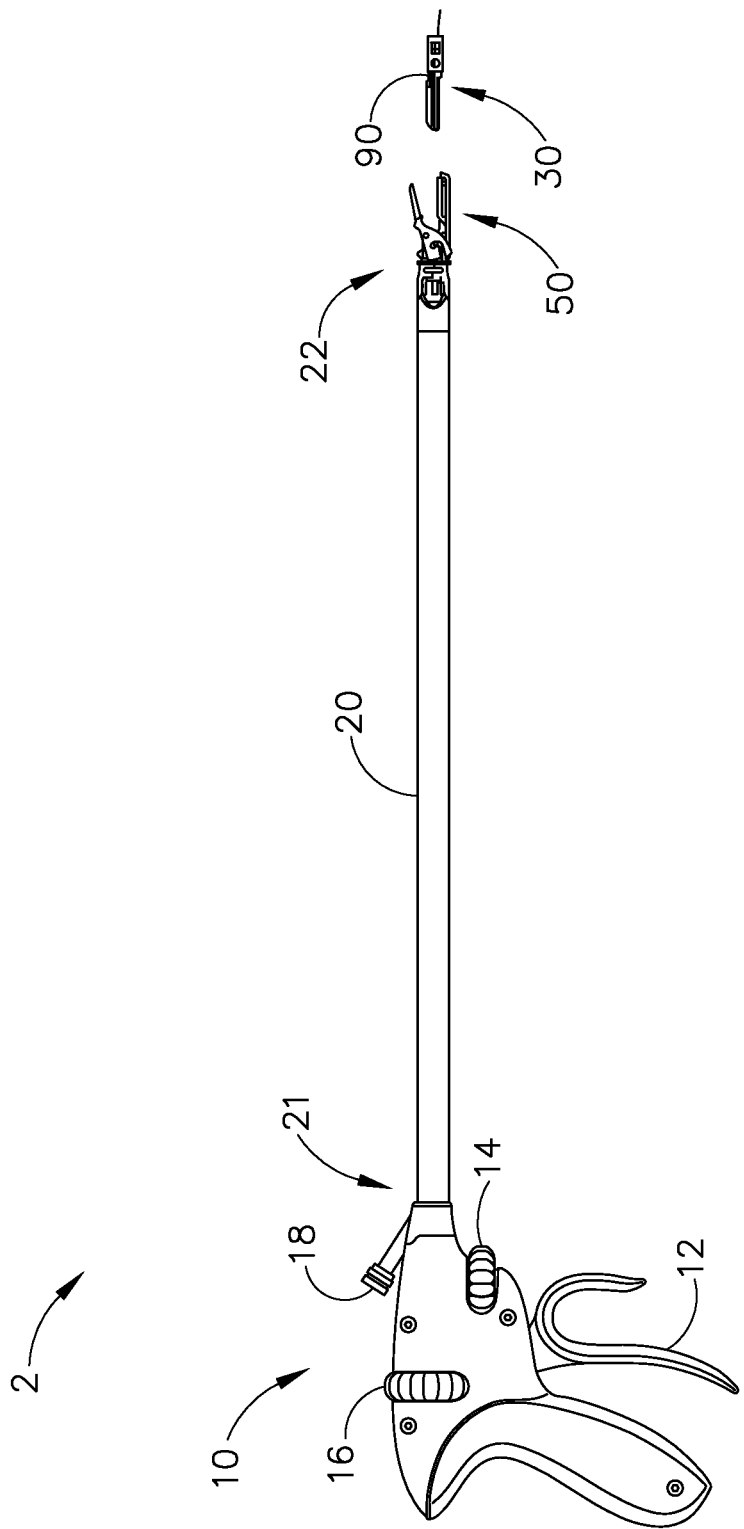
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Surgical Suturing Instrument

FIG. 1 illustrates an example of a surgical suturing instrument (2). Instrument (2) comprises a handle assembly (10), an elongate shaft (20), and a cartridge receiving assembly (50), which is operable to receive a needle applier cartridge (30). Shaft (20) has a proximal end (21), a distal end (22), and a longitudinal axis extending therebetween. Handle assembly (10) is connected to the proximal end (21) of the shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to the distal end (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first input (12), shown here as a trigger that pivots between opened and closed positions, may be used to selectively actuate needle applier cartridge (30). The trigger may be spring biased to return the trigger to its open position. A second input (14), shown here as a rotary knob, may be used to selectively articulate shaft (20). A third input (16), shown here as a rotary knob, may be used to selectively rotate needle applier cartridge (30) about shaft (20). Of course, the number, type, configuration, and operation of inputs (12, 14, 16) may vary.

Figure 2A:
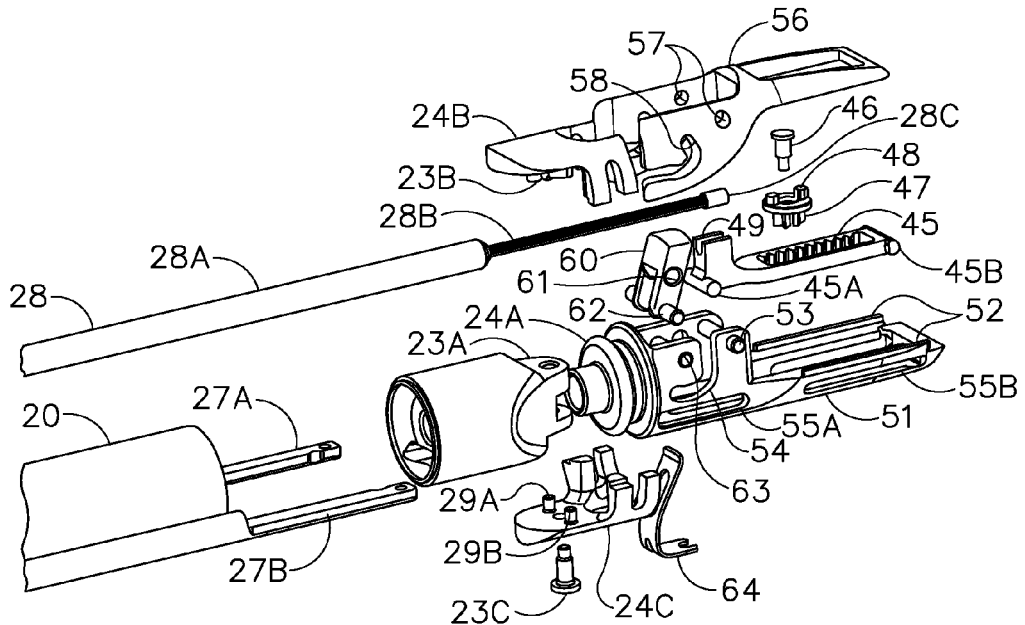
FIG. 2A depicts top perspective exploded view of a cartridge receiving assembly of the instrument of FIG. 1.
Figure 2B:
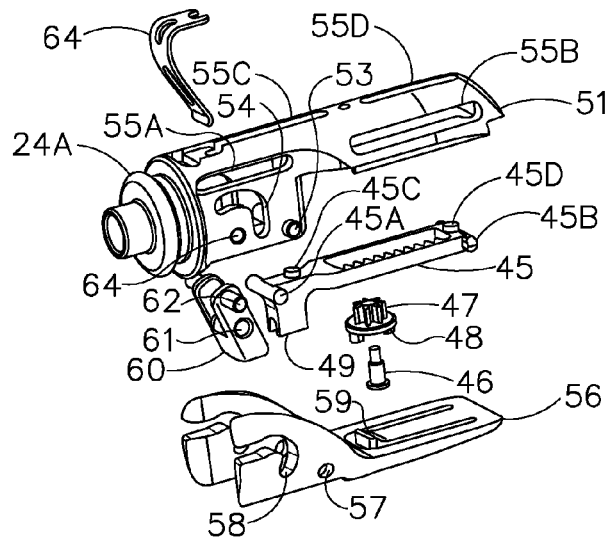
FIG. 2B depicts bottom perspective exploded view of the cartridge receiving assembly of FIG. 2A.

FIGS. 2A-2B illustrate exploded views of cartridge receiving assembly (50) of the present example. Distal end (22) of shaft (20) comprises an articulation joint (23) and a rotational bearing (24). Articulation joint (23) includes a knuckle (23A) that receives pins (23B, 23C), which are connected to bearing supports (24B, 23C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to rotary knob (14) to opposingly push and pull rods (27A, 27B). In other words, rotary knob (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by the pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first input (12) and to third input (16). Actuation of first input (12) will impart axial push and pull loads on drive rod (28) to longitudinally reciprocate rack (45) and thereby actuate needle applier cartridge (30). Actuation of third input (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the closed configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
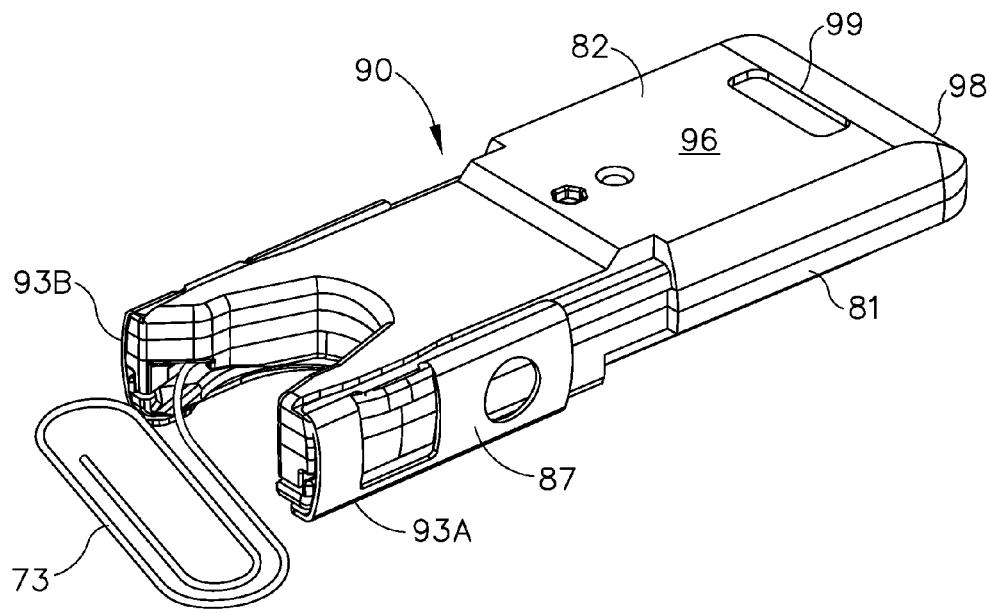
FIG. 3A depicts a top perspective view of an exemplary cartridge configured for receipt in the cartridge receiving assembly of FIG. 2A.
Figure 3B:
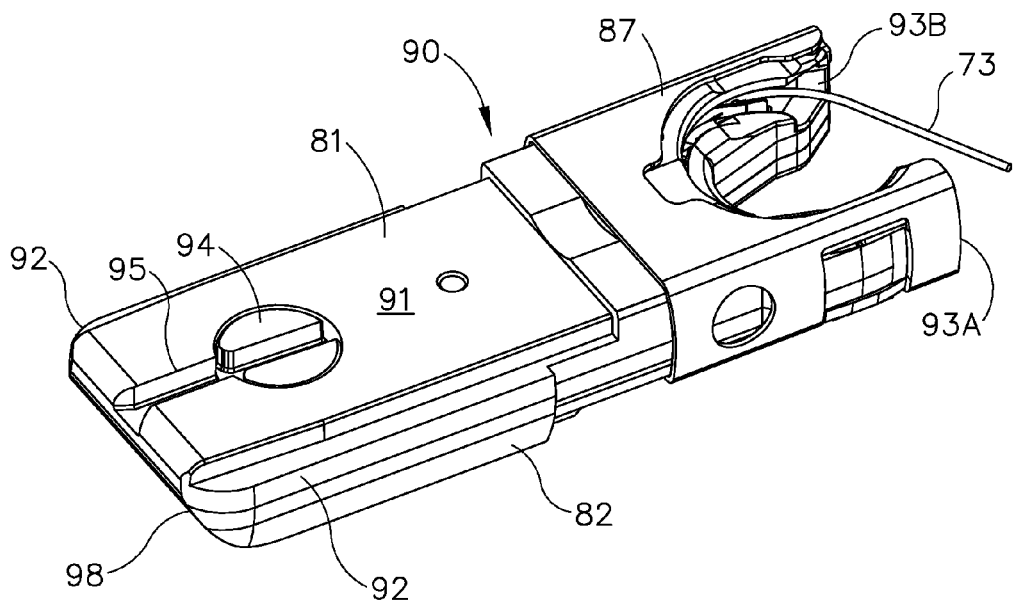
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
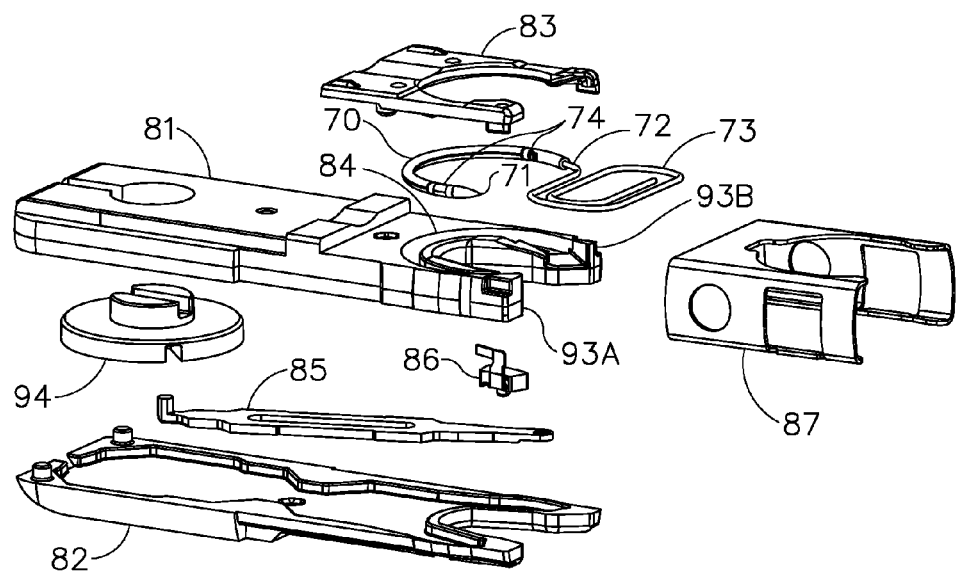
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from the trailing end (72). Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
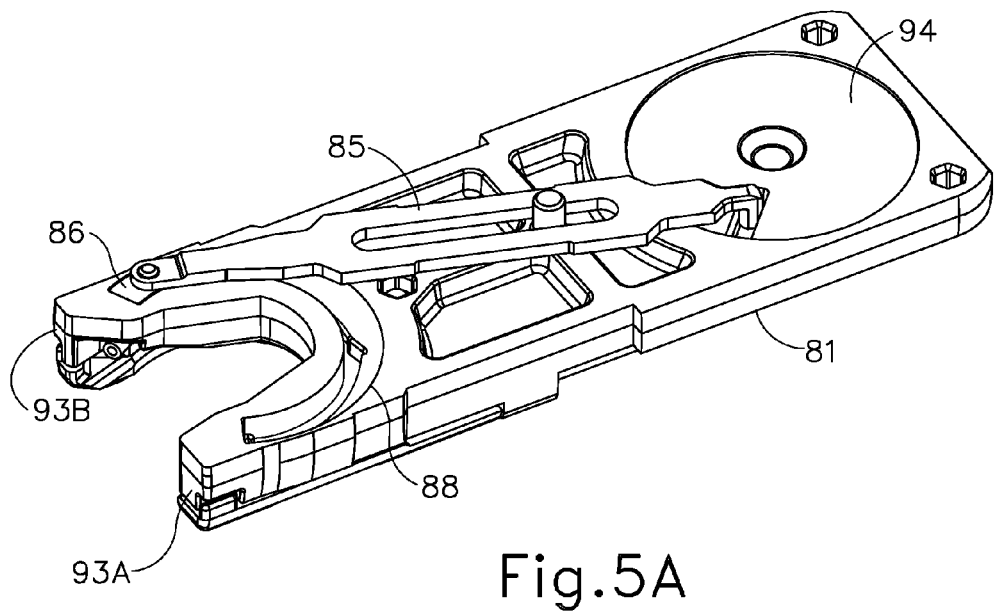
FIG. 5A depicts a perspective view of a drive assembly of the cartridge of FIG. 3A, with the drive assembly at one end of its stroke.
Figure 5B:
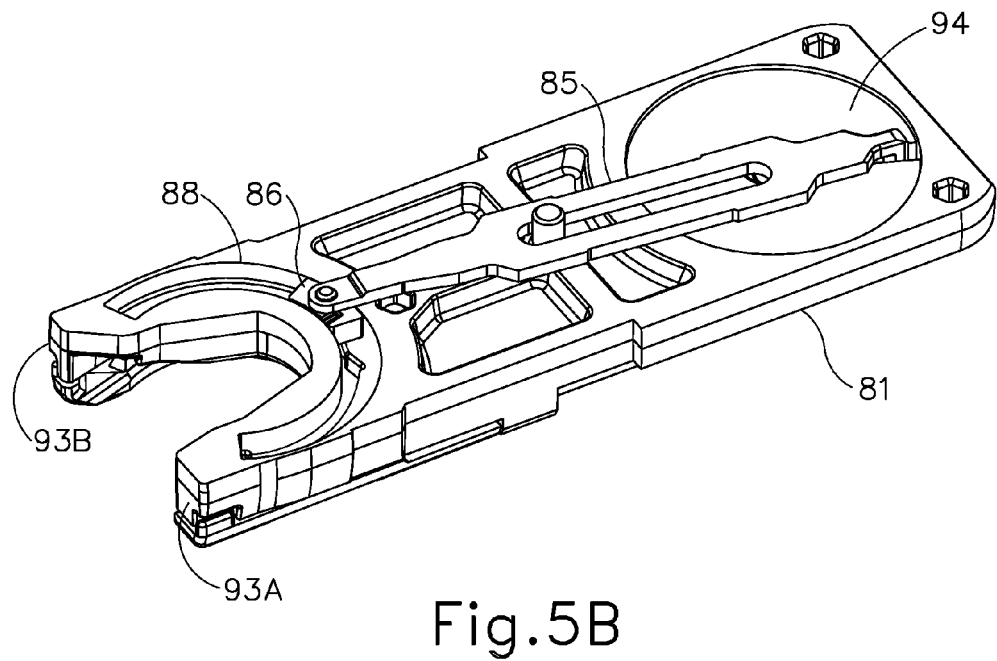
FIG. 5B depicts a perspective view of the drive assembly of FIG. 5A, with the drive assembly at mid-stroke.
Figure 5C:
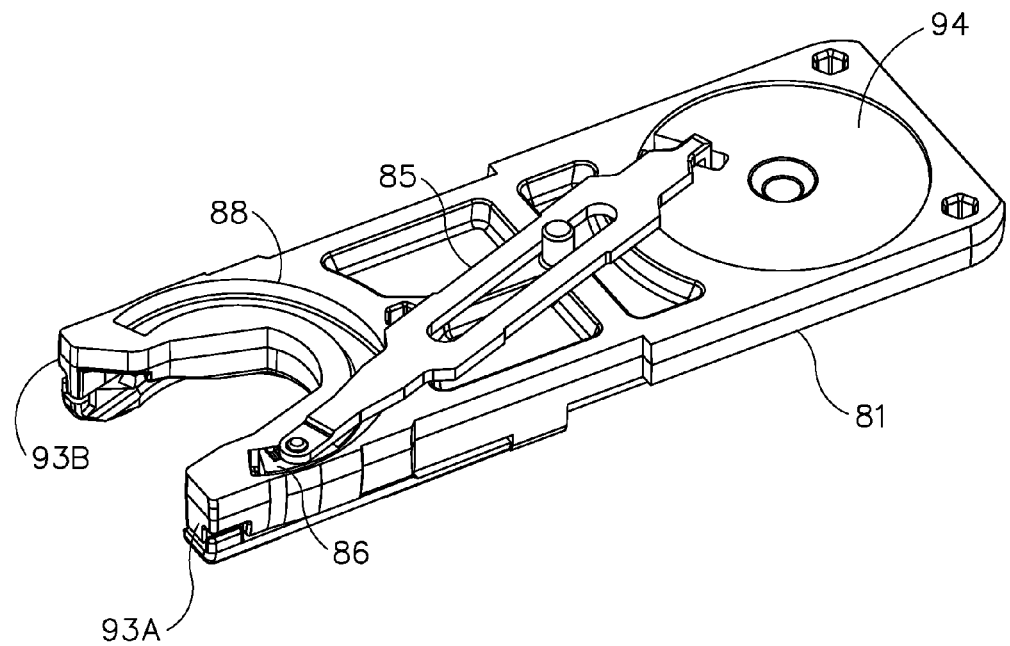
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) omitted from FIGS. 5B-5C. Needle driver (86) rides in a carrier track (88) and extends into needle track (84) to engage and drive needle (70). A link (85) connects rotary input (94) to needle driver (86). FIG. 5A shows needle driver (86) positioned at one end of its stroke in carrier track (88). As shown in FIG. 5B, counter-clockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counter-clockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
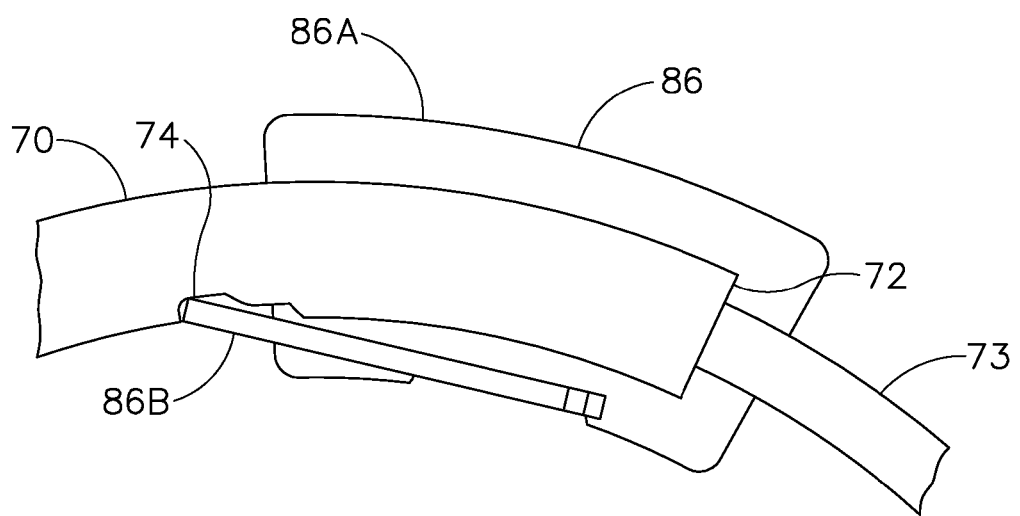
FIG. 6 depicts a partial plan view of a needle driver of the cartridge of FIG. 3A engaging a needle of the cartridge of FIG. 3A.
Figure 7:
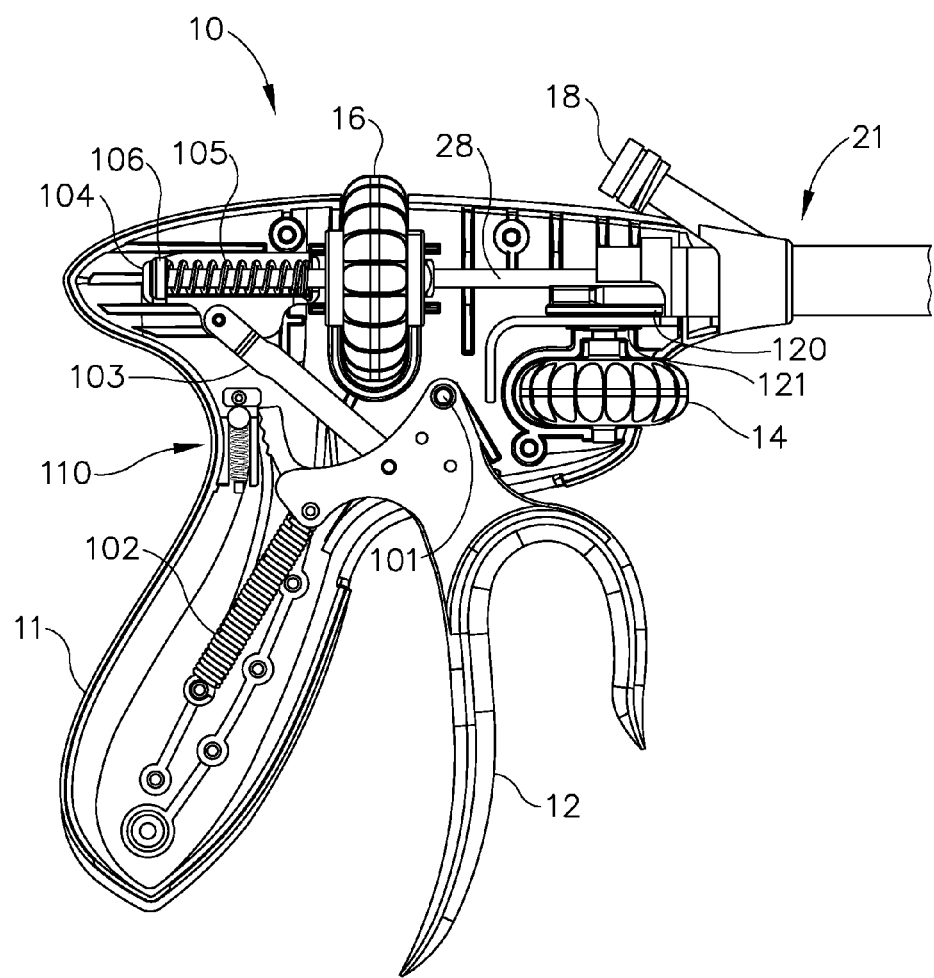
FIG. 7 depicts a side elevational view of the handle assembly of the instrument of FIG. 1, with a housing half removed to reveal internal components.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (75) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C, when first input (12) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (95) and entrance port (97). Tissue interposed between arms (93A, 93B) will be pierced by leading end (71) of needle (70).

When first input (12) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first input (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) will follow needle (70) and be threaded through the pierced tissue.

When first input (12) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first input (12) being actuated twice. The sequence may be repeated as needed by the surgeon to achieve the desired suturing task.

Figure 8:
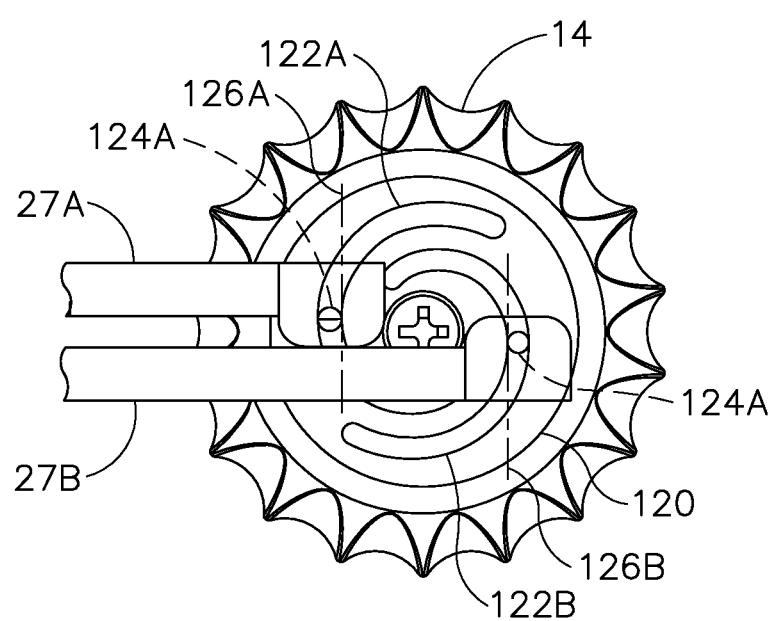
FIG. 8 depicts a top plan view of an articulation control assembly of the handle assembly of FIG. 7.

Rotary knob (14) is operable to selectively articulate joint (23). Rotary knob (14) rotates in a plane spaced below and generally parallel with shaft (20). An axle (121) connects rotary knob (14) to a disk (120) in shroud (11) that also rotates in a plane generally parallel with the shaft (20). As shown in FIG. 8, disk (120) comprises first and second cam slots (122A, 122B), each having a length with angular and radial components. In this embodiment, the cam slots (122A, 122B) are two identical spirals offset 180 degrees from one another. Each cam slot (122A, 122B) has an angular span between about 220 degrees and about 300 degrees, with their angular spans overlapping one another. Cam slots (122A, 122B) also increase their distance from the center of disk (120) in the same angular direction. Each cam slot (122A, 122B) has a radial span of about 0.100 inches and about 0.155 inches. Of course, the configuration and dimensions of cam slots (122A, 122B) may alternatively differ from the foregoing.

Figure 11C:
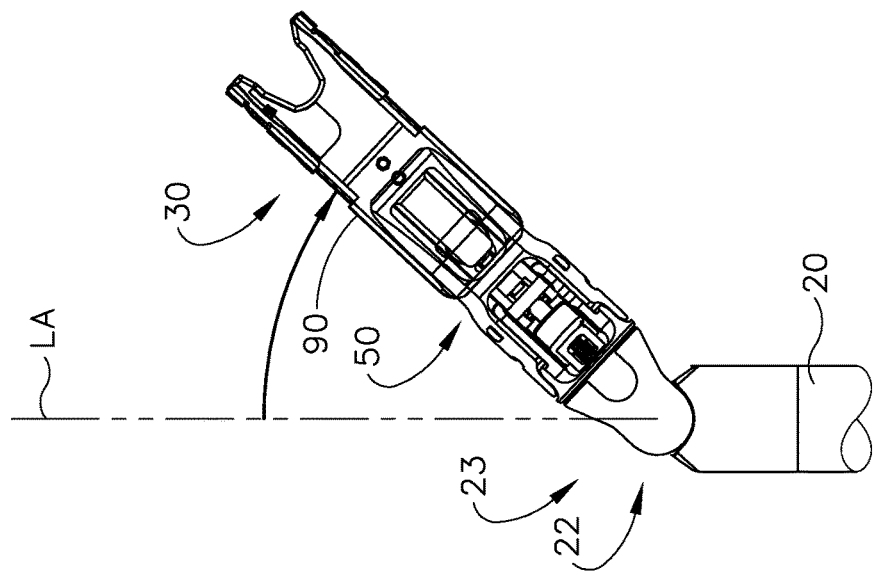
FIG. 11C depicts a top plan view of the cartridge receiving assembly of FIG. 2A, the cartridge of FIG. 3A, and the shaft assembly of the instrument of FIG. 1, with the cartridge receiving assembly deflected in a second direction away from the longitudinal axis of the shaft assembly by the articulation control assembly of FIG. 8.
Figure 11B:
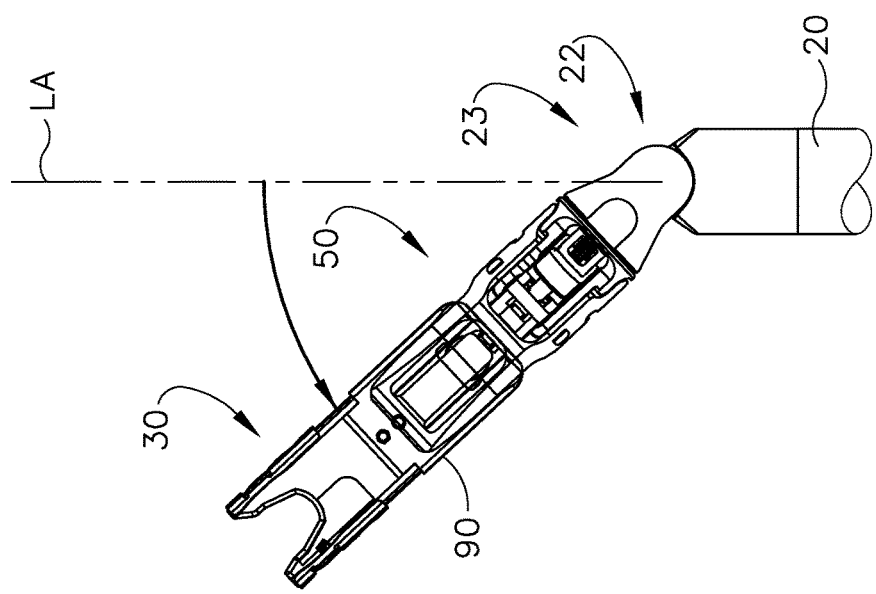
FIG. 11B depicts a top plan view of the cartridge receiving assembly of FIG. 2A, the cartridge of FIG. 3A, and the shaft assembly of the instrument of FIG. 1, with the cartridge receiving assembly deflected in a first direction away from the longitudinal axis of the shaft assembly by the articulation control assembly of FIG. 8.
Figure 11A:
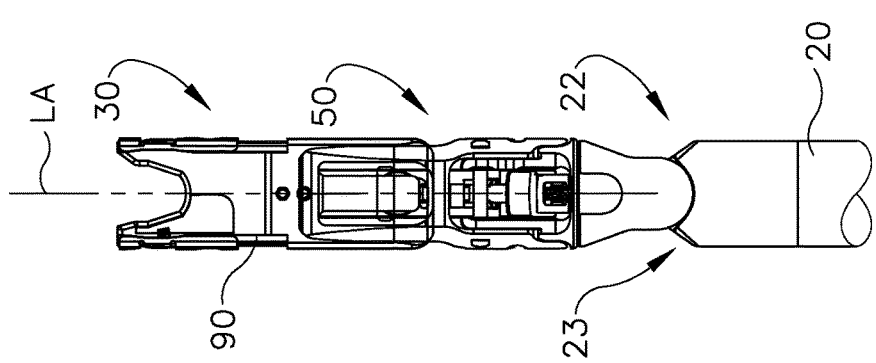
FIG. 11A depicts a top plan view of the cartridge receiving assembly of FIG. 2A, the cartridge of FIG. 3A, and the shaft assembly of the instrument of FIG. 1, with the cartridge receiving assembly aligned with the longitudinal axis of the shaft assembly.
Figure 12:
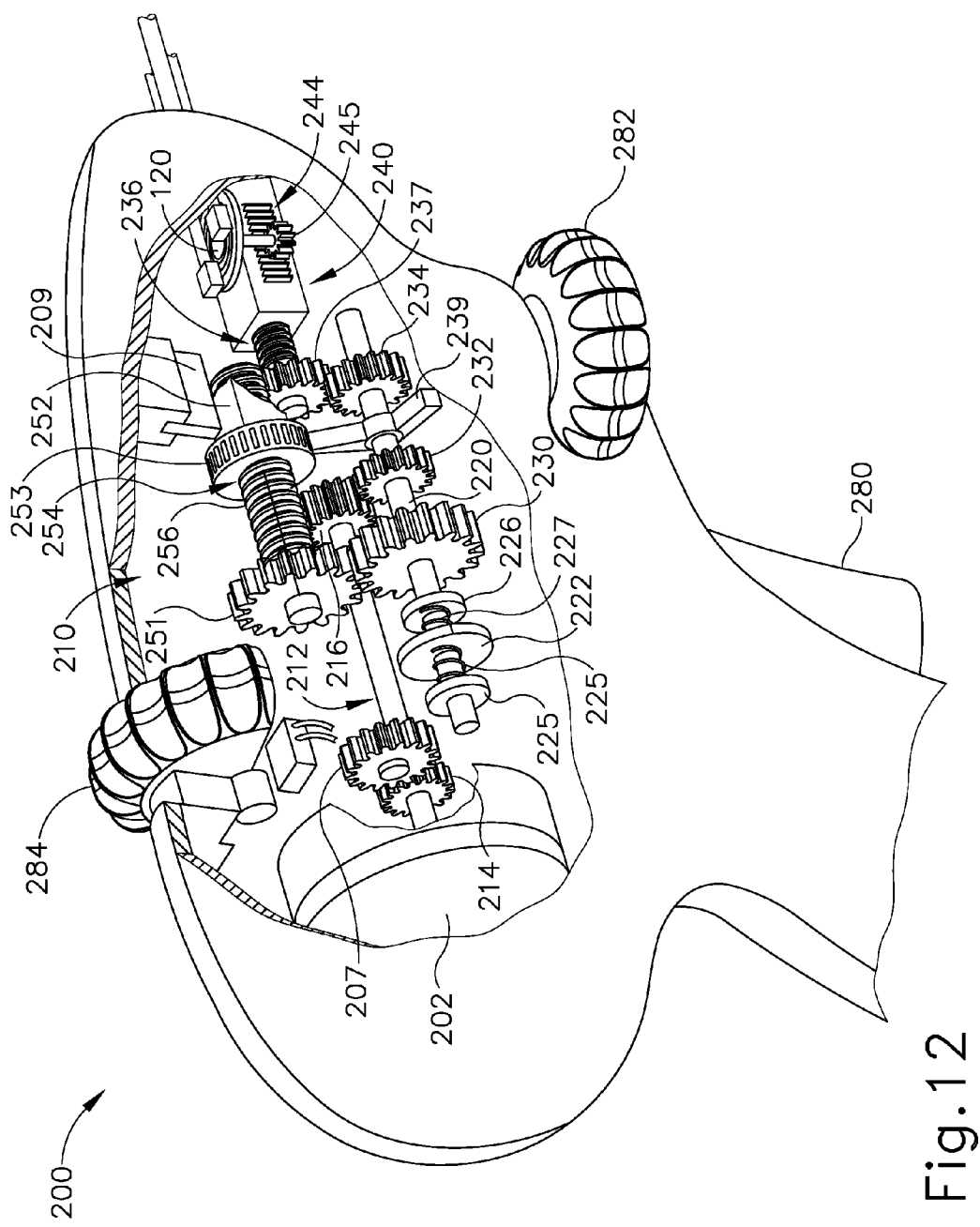
FIG. 12 depicts an exemplary alternative handle assembly that may be incorporated into the instrument of FIG. 1.

Cam slot (122A) receives a cam follower (124A) on a distal half of disk (120), and cam slot (122B) receives a cam follower (124B) on the proximal half of disk (120). Followers (124A, 124B) extend downwardly and generally normal from the proximal ends of rods (27A, 27B), respectively. In this example, followers (124A, 124B) are medially offset from longitudinal axes of the respective drive rod (27A, 27B). Rods (27A, 27B) are constrained to slide axially, so counterclockwise rotation of disk (120) moves rod (27B) proximally and simultaneously moves rod (27A) distally to articulate joint (23) to the left of the longitudinal axis (LA) of shaft (20), as shown in the transition from FIG. 11A to FIG. 11B. Similarly, clockwise rotation of disk (120) moves rod (27B) distally and simultaneously moves rod (27A) proximally, thereby articulating joint (23) to the right of the longitudinal axis (LA) of shaft (20), as shown in the transition from FIG. 11A to FIG. 11C.

Cam slots (122A, 122B) each define a tangent axis (126A, 126B) where cam slot (122A, 122B) is engaged by the respective cam followers (124A, 124B). The tangent axes (126A, 126B) may be substantially normal to the longitudinal axes of rods (27A, 27B) so axial push and pull loads on rods (27A, 27B) introduced by side loads on cartridge receiving assembly (50) will not cause disk (120) to rotate. Accordingly, joint (23) will remain locked at its articulated angle. Frictional interfaces or detents may be added to further prevent unintentional articulation, such as between followers (124A, 124B) and cam slots (122A, 122B), between disk (120) and shroud (11), between axle (121) and shroud (11), and/or in any other suitable fashion.

Figure 9:
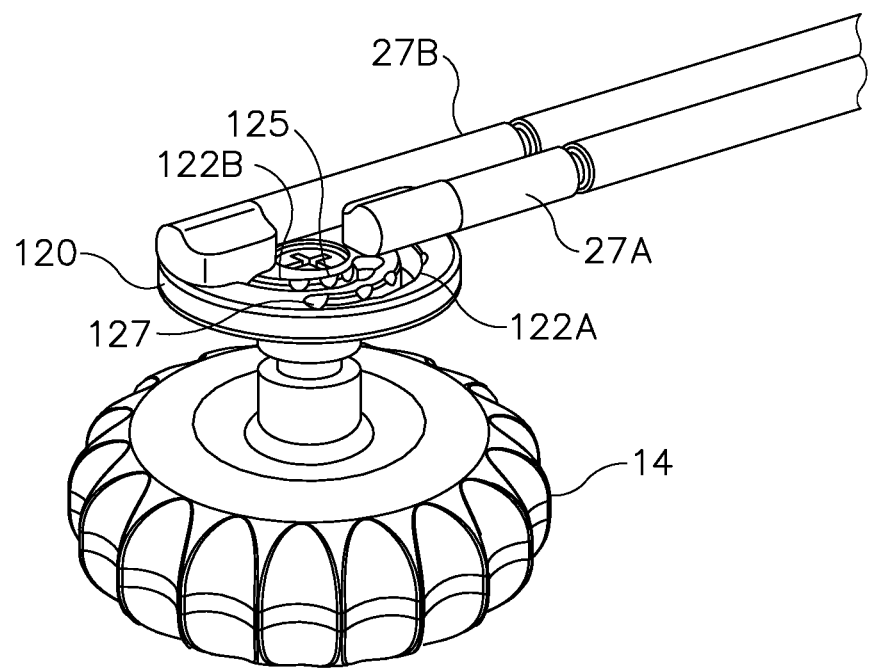
FIG. 9 depicts a perspective view of the articulation control assembly of FIG. 8.

FIG. 9 illustrates an alternative example of an articulation control. A plurality of detents (125) are positioned along cam slots (122A, 122B). In addition to preventing unintentional articulation, detents (125) may provide feedback to the surgeon indicating various angular positions of needle applier cartridge (30) relative shaft (20). Detents (125) may be indexed to correspond to one or more predetermined articulation angles, such as 0 degrees, 15 degrees, 45 degrees, and the like; or detents (125) may be equally distributed along cam slots (122A, 122B). Larger detents (127) may be located at the ends of the cam slots (122A, 122B).

Figure 10:
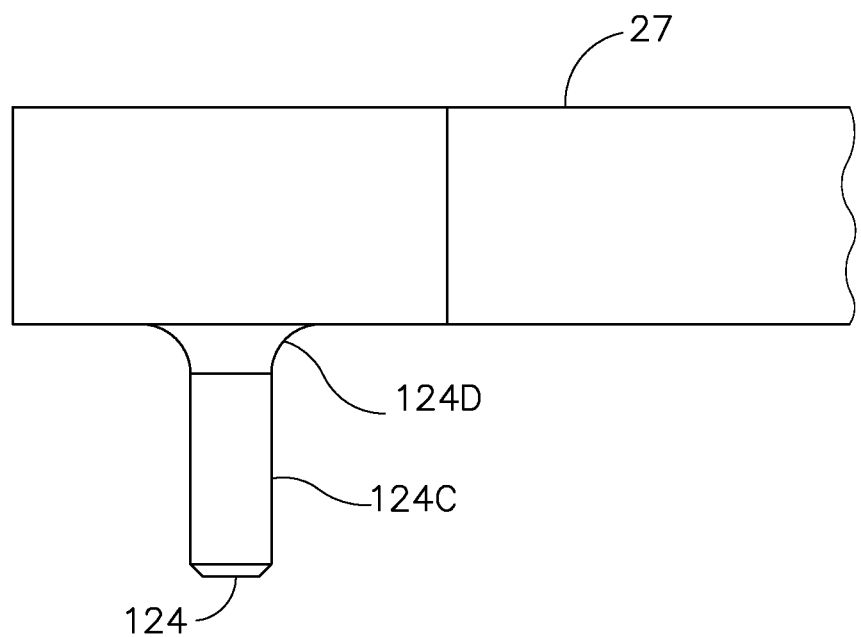
FIG. 10 depicts a side elevational view of an articulation rod and follower of the articulation control assembly of FIG. 8.

Detents (125) open to the top surface of disk (120), but only partially extend into cam slots (122A, 122B). As shown in FIG. 10, follower (124) extends downwardly from articulation rod (27). Follower (124) includes a straight portion (124C) that closely fits in cam slots (122A, 122B) and a radius portion (124D) dimensioned to be received by detents (125). As disk (120) rotates, radius portion (124D) will raise and lower into detents (125) but the straight portion (124C) will follow and remain engaged in the cam slots (122A, B). In some versions, rod (27) will be biased downwardly toward disk (120) to provide a tactile and/or audible "click" as radius portion (124D) engages detents (125).

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, now U.S. Pat. No. 9,357,998, issued on Jun. 7, 2016, the disclosure of which is incorporated by reference herein; U.S. patent application Ser. No. 14/297,993, entitled "Jawed Cartridge Receiving Assembly for Needle Cartridge," filed Jun. 6, 2014, published as now U.S. Pub. No. 2016/0046096 on Feb. 18, 2016, the disclosure of which is incorporated by reference herein; and U.S. patent application Ser. No. 14/298,038, entitled "Circular Needle Applier with Cleats," filed Jan. 30, 2015, now U.S. Pat. No. 9,375,212, issued on Jun. 28, 2016, the disclosure of which is incorporated by reference herein. It should be understood that such details, explanations, examples, and alternative embodiments may be readily applied to the above-described instrument (10) and subcomponents thereof.

II. Exemplary Handle Assembly with Motorized Actuation Components

In some instances, it may be desirable to actuate needle applier cartridge (30), to articulate shaft (20), and/or to rotate needle applier cartridge (30) about shaft (20) in a way that avoids manually driving surgical suturing instrument (2). For instance, in the event that the operator has inadequate hand strength to actuate needle applier cartridge (30), to articulate shaft (20), and/or to rotate needle applier cartridge (30), it may be desirable to provide a motorized assembly for instrument (2). Motorizing at least part of instrument (2) may also reduce the risk of operator error in actuating needle applier cartridge (30), articulating shaft (20), and/or rotating needle applier cartridge (30). For instance, in some cases, operator error with a manually driven instrument (2) may result in needle applier cartridge (30) failing to actuate fully. This may occur when an operator fails to fully manually actuate first input (12), which may result in needle (70) not being fully actuated through its drive stroke. Thus, motorizing the actuating of needle applier cartridge (30) may ensure that needle (70) is fully driven through tissue interposed between arms (93A, 93B).

In some versions of instrument (2) that provide motorization of at least two of the above-noted functionalities, it may be desirable to motorize such functionalities with just one single motor. For instance, handle assembly (10) may include a transmission assembly that may be shifted between three states by a double acting solenoid or some other shifting mechanism, allowing a single motor to be used to drive actuation of needle applier cartridge (30), articulation of shaft (20), and/or to rotation of needle applier cartridge (30). Various examples of how instrument (2) may be reconfigured to incorporate a motor will be described in greater detail below; while other examples will be apparent to those of ordinary skill in the art according to the teachings herein. It should be understood that the examples described below may function substantially similar to instrument (2) described above. In particular, the surgical suturing instruments described below may be used to suture tissue.

A. Exemplary Motorized Drive Assembly

FIGS. 12-19 illustrate an exemplary handle assembly (200) that is operable for use with instrument (2) discussed above. Handle assembly (200) is connected to the proximal end (21) of the shaft (20). In this example handle assembly (200) includes a motor (202) and a transmission assembly (210). As will be described in more detail below, motor (202) is configured to drive actuation of needle applier cartridge (30), articulation of shaft (20), and rotation of needle applier cartridge (30) via transmission assembly (210). In particular, and also as will be described in more detail below, transmission assembly (210) may be shifted between three states by a double acting solenoid (204), so as to allow motor (202) to be used to drive actuation of needle applier cartridge (30), articulation of shaft (20), and rotation of needle applier cartridge (30). It should be appreciated that handle assembly (200), however, may additionally include a variety of manual actuators including but not limited to a manual pistol grip handle, a scissor grip handle, a syringe grip handle, endoscopic rotary knobs, and the like. Handle assembly (200) could also take the form of a robotic interface, such as a DAVINCI puck, or a housing comprising gears or pulleys, servomechanisms, and the like. The shaft (20), cartridge receiving assembly (50), and cartridge (30) that are used with handle assembly (200) may be identical to the shaft (20), cartridge receiving assembly (50), and cartridge (30) that are used with handle assembly (10) as described above.

Figure 15A:
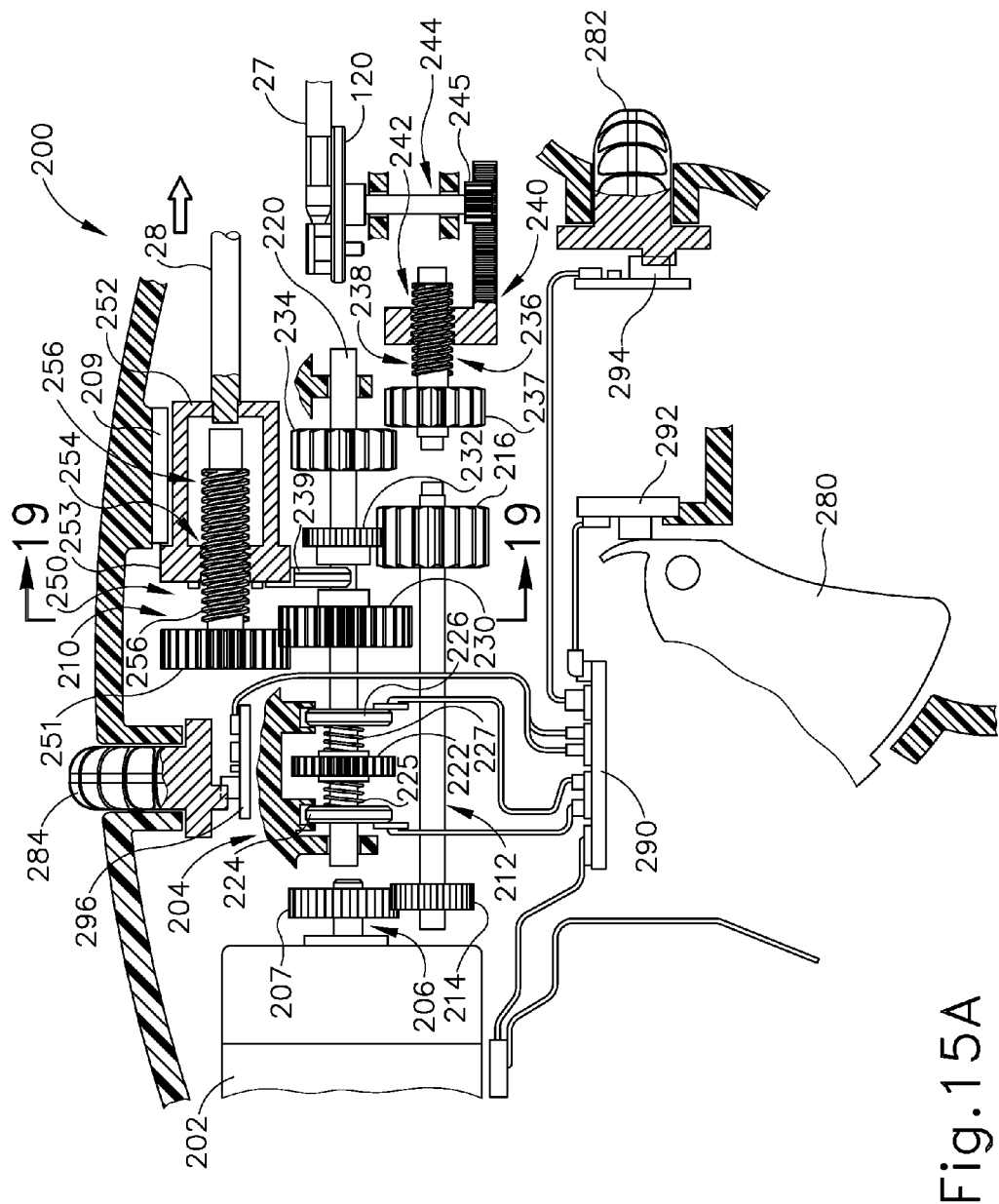
FIG. 15A depicts a side elevational view of the handle assembly of FIG. 12, with portions of the handle assembly in cross-section, showing the handle in an end effector actuation state, with an actuation rod in a proximal position.
Figure 15B:
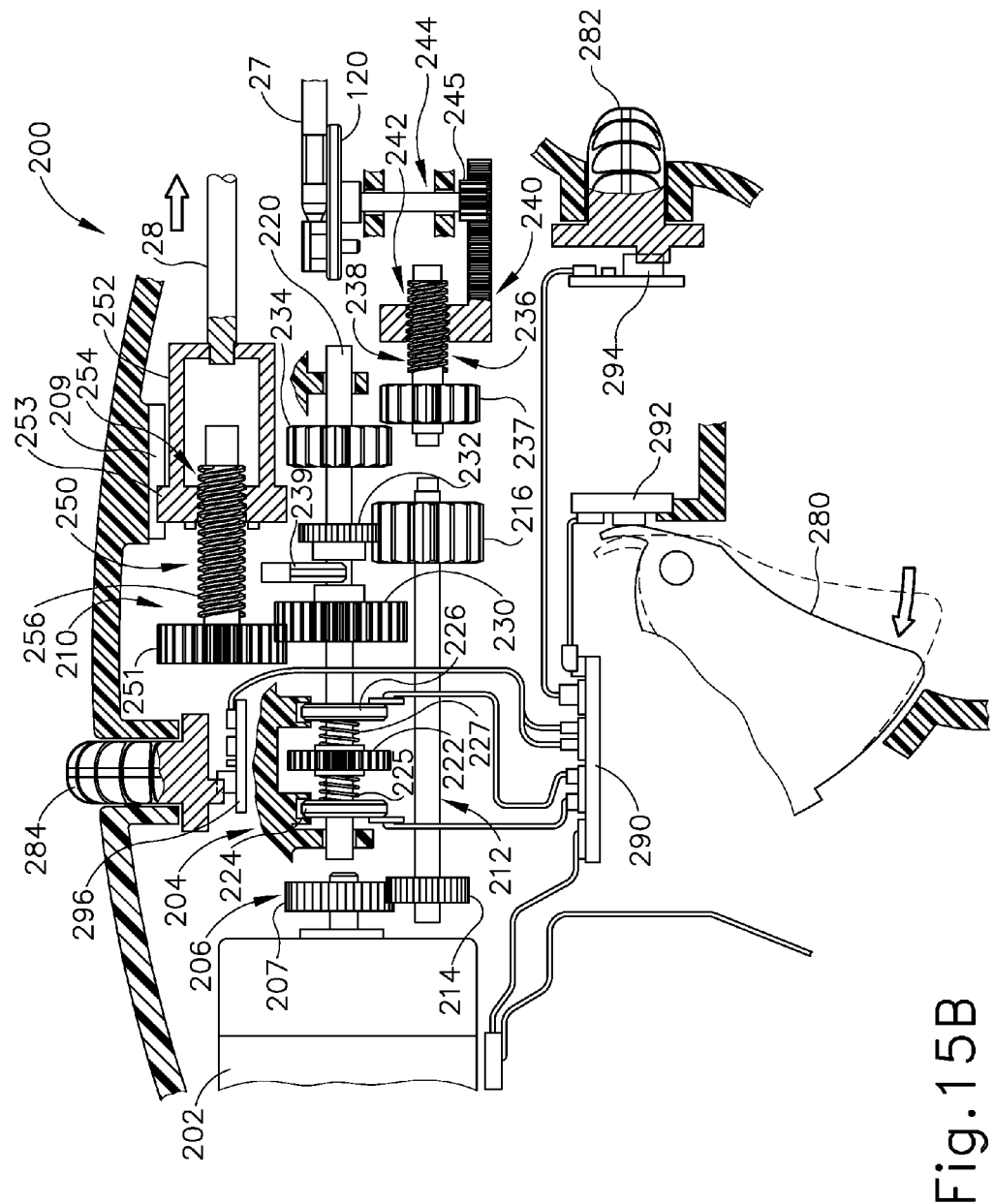
FIG. 15B depicts a side elevational view of the handle assembly of FIG. 12, with portions of the handle assembly in cross-section, showing the handle in the end effector actuation state, with the actuation rod in a distal position.
Figure 16:
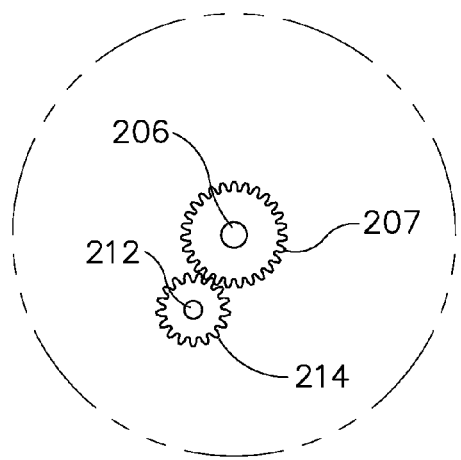
FIG. 16 depicts a cross-sectional view of drive components of the handle assembly of FIG. 12, taken along line 16-16 of FIG. 13.

As best seen in FIGS. 13-16 and Motor (202) includes a drive shaft (206). Activation of motor (202) causes rotation of drive shaft (206). Drive shaft (206) includes a gear (207) having a plurality of teeth angularly disposed about and radially extending from an exterior surface of gear (207). Transmission assembly (210) includes an axle (212). Axle (212) is rotatably secured within and to handle assembly (200) such that axle (212) is operable to rotate within and relative to handle assembly (200). Axle (212) includes a pair of gears (214, 216) that are fixedly secured to axle (212). Gear (214) includes a plurality of teeth that are angularly disposed about and radially extending from an exterior surface of gear (214). Gear (216) includes a plurality of teeth that are angularly disposed about and radially extending from an exterior surface of gear (216). As best seen in FIG. 16, the teeth of gear (207) of drive shaft (206) are engaged with the teeth of first gear (214) of axle (212) such that rotation of drive shaft (206) causes concurrent rotation of axle (212).

Figure 13:
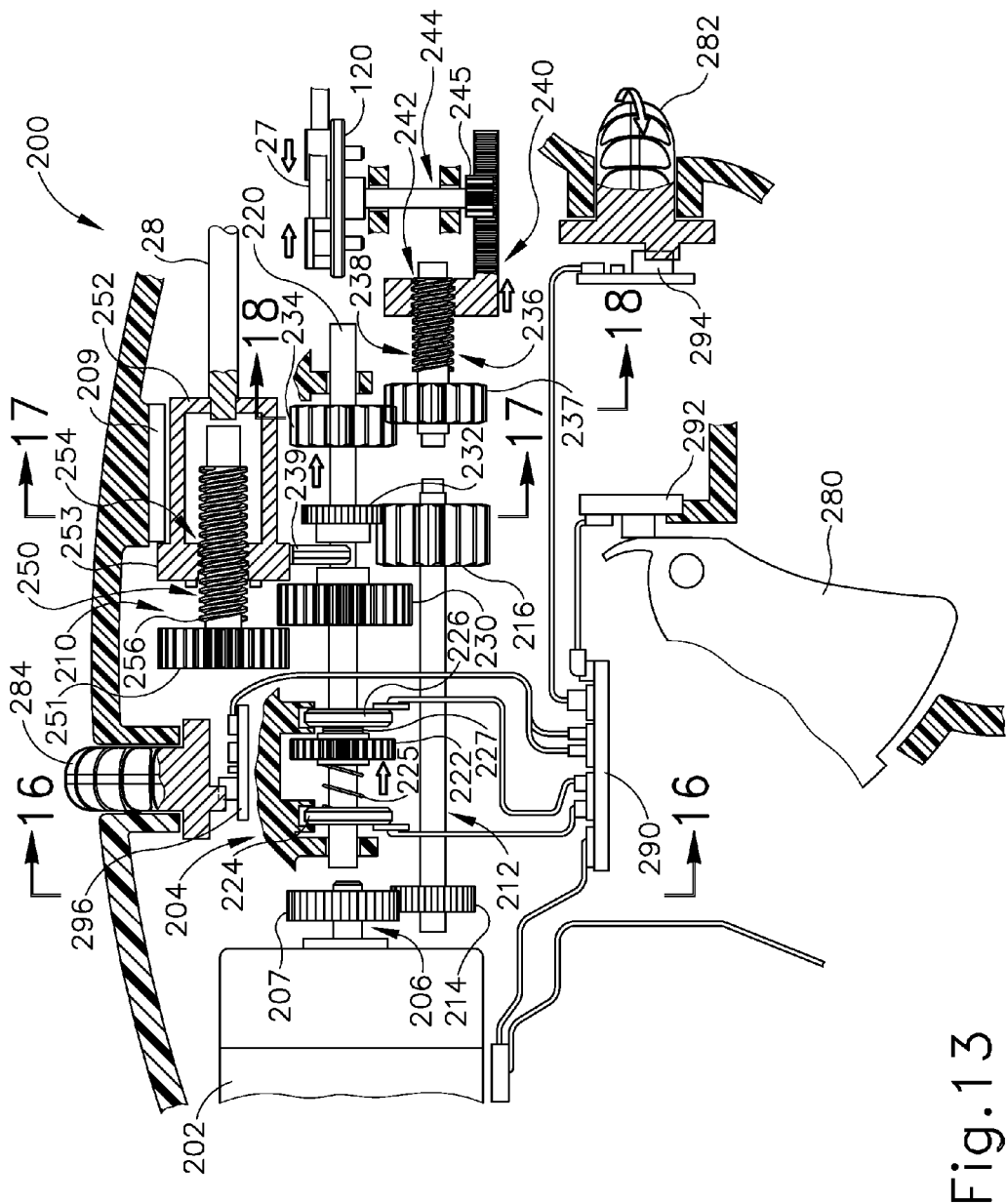
FIG. 13 depicts a side elevational view of the handle assembly of FIG. 12, with portions of the handle assembly in cross-section, showing the handle in an articulation control state.
Figure 14:
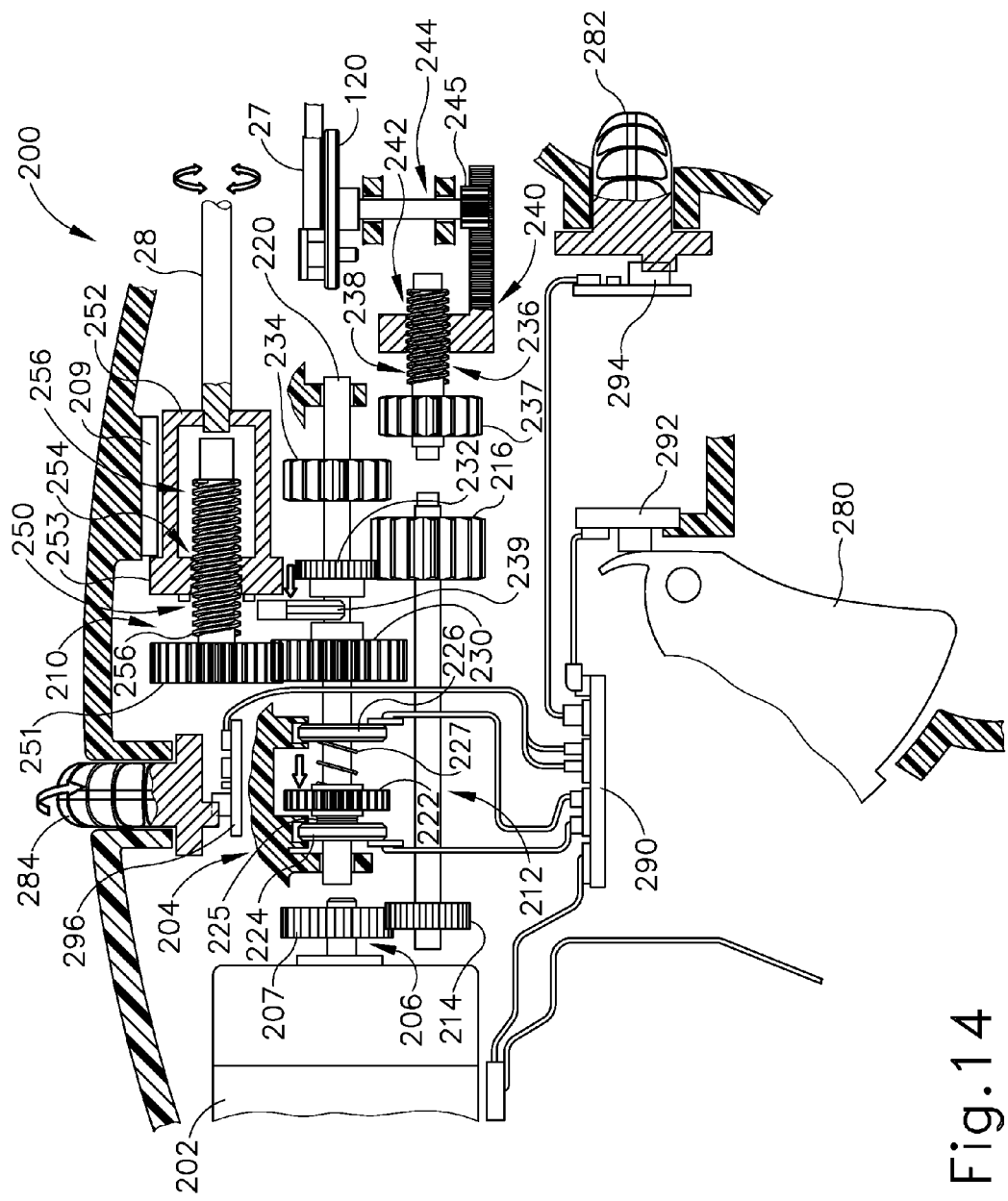
FIG. 14 depicts a side elevational view of the handle assembly of FIG. 12, with portions of the handle assembly in cross-section, showing the handle in a distal head rotation control state.

Solenoid (204) includes a piston (220). Piston (220) is rotatably and slidably secured within and to handle assembly (200) such that piston (212) is operable to rotate and translate within and relative to handle assembly (200). A magnet (222) is fixedly secured to a proximal end of piston (220) such that translation of magnet (222) will cause translation of piston (220). Solenoid (204) further includes a pair of wire coils (224, 226) positioned about the proximal end of piston (220) such that piston (220) is operable to rotate and translate within and relative to wire coils (224, 226). Magnet (222) of piston (220) is positioned between wire coils (224, 226). Magnet (222), and as a result piston (220), is biased toward an intermediate position (FIGS. 15A and 15B) via a pair of coil springs (225, 227), which are coaxially positioned about piston (220) and between wire coils (224, 226) and magnet (222). As will be described in more detail below, when an electric current is provided through wire coils (224, 226), wire coils (224, 226) are configured to cause proximal and distal translation of magnet (222), thereby causing proximal and distal translation of piston (220). In particular, when an electric current is provided through wire coil (224), wire coil (224) is configured to cause proximal translation of magnet (222), and as a result piston (220) (FIG. 14); and when an electric current is provided through wire coil (226), wire coil (226) is configured to cause distal translation of magnet (222), and as a result piston (220) (FIG. 13). Alternatively, when an electric current is provided through wire coil (224), wire coil (224) is configured to cause distal translation of magnet (222), and as a result piston (220) (FIG. 13); and when an electric current is provided through wire coil (226), wire coil (226) is configured to cause proximal translation of magnet (222), and as a result piston (220) (FIG. 14).

Figure 17:
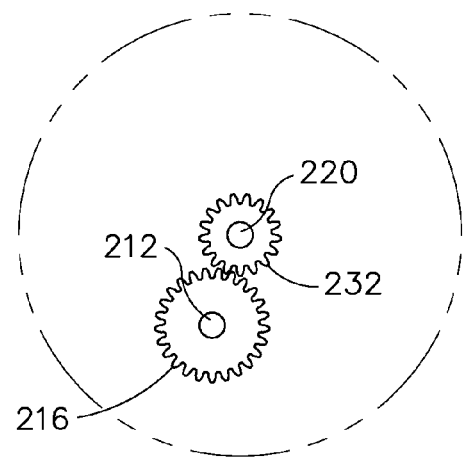
FIG. 17 depicts a cross-sectional view of drive components of the handle assembly of FIG. 12, taken along line 17-17 of FIG. 13.

Piston (220) further includes a plurality of gears (230, 232, 234) that are fixedly secured to piston (220). Gear (230) includes a plurality of teeth angularly disposed about and extending radially from an exterior surface of gear (230). Gear (232) includes a plurality of teeth angularly disposed about and extending radially from an exterior surface of gear (232). Gear (234) includes a plurality of teeth angularly disposed about and extending radially from an exterior surface of gear (234). As best seen in FIG. 17, the teeth of gear (216) of axle (212) are engaged with the teeth of gear (232) of piston (220) such that rotation of axle (212) causes concurrent rotation of piston (220). Gear (216) of axle (212) is of sufficient width such that as piston (220) and gear (232) translate between the proximal position (FIG. 14), the intermediate position (FIGS. 15A and 15B), and the distal position (FIG. 13), gear (232) remains engaged with gear (216) such that rotation of axle (212) causes concurrent rotation of piston (220) as piston (220) translates between the proximal position (FIG. 14), the intermediate position (FIGS. 15A and 15B), and the distal position (FIG. 13).

As shown in FIGS. 12-15B, transmission assembly (210) further includes a threaded member (236). Threaded member (236) is rotatably secured within and to handle assembly (200) such that threaded member (236) is operable to rotate within and relative to handle assembly (200). Threaded member (236) includes an integral gear (237) having a plurality of teeth angularly disposed about and extending radially from an exterior surface of gear (237). As shown in FIG. 13, when piston (220) is driven to the distal position by solenoid (204), the teeth of gear (234) of piston (220) are engaged with the teeth of gear (237) of threaded member (236) such that rotation of piston (220) causes concurrent rotation of threaded member (236). Transmission assembly (210) further includes a rack (240). Rack (240) is slidably secured within and to handle assembly (200) such that rack (240) is operable to translate within and relative to handle assembly (200). Rack (240) includes a plurality of teeth disposed along a length of and extending laterally from rack (240). Rack (240) further includes a threaded bore (242) configured to matingly receive threading (238) of threaded member (236) such that rotation of threaded member (236) causes translation of rack (240).

Figure 18:
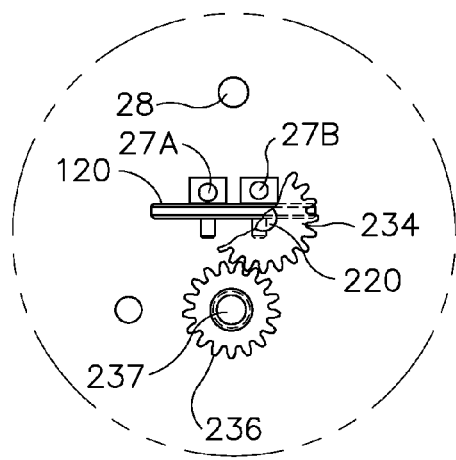
FIG. 18 depicts a cross-sectional view of drive components of the handle assembly of FIG. 12, taken along line 18-18 of FIG. 13.

Disk (120) of the present example includes a drive shaft (244), which is rotatably supported in handle assembly (200). Rotation of drive shaft (244) causes rotation of disk (120). Drive shaft (244) includes a gear (245) having a plurality of teeth angularly disposed about and extending radially from an exterior surface of gear (245). The teeth of gear (245) are engaged with the teeth of rack (240) such that translation of rack (240) causes rotation of drive shaft (244), thereby causing rotation of disk (120). As shown in FIG. 18, rods (27A, 27B) are engaged with disk (120). As discussed above with reference to a similar configuration shown in FIGS. 8-9, rotation of disk (120) will cause opposing longitudinal translation of rods (27A, 27B) which will thereby cause articulation of joint (23). It should therefore be understood that with piston (120) in the distal position (FIG. 13), motor (120) is operable to selectively drive articulation of joint (23).

Transmission assembly (210) further includes another threaded member (250). Threaded member (250) is rotatably secured within and to handle assembly (200) such that threaded member (250) is operable to rotate within and relative to handle assembly (200). Threaded member (250) includes a gear (251) having a plurality of teeth angularly disposed about and extending radially from an exterior surface of gear (251). As shown in FIG. 13, with piston (220) in the distal position, the teeth of gear (251) of threaded member (250) are disengaged from the teeth of gear (230) of piston (220) such that rotation of piston (220) does not cause concurrent rotation of threaded member (250). As shown in FIG. 14, however, with piston (220) moved into the proximal position, the teeth of gear (251) of threaded member (250) are engaged with the teeth of gear (230) of piston (220) such that rotation of piston (220) causes concurrent rotation of threaded member (250).

Drive rod (28) includes a sleeve (252). Sleeve (252) is unitarily secured to the proximal end of drive rod (28) and extends proximally from the proximal end of drive rod (28). Sleeve (252) includes an integral spline feature (253) and a threaded bore (254). Spline feature (253) includes an angularly spaced array of radially and longitudinally extending splines. Threaded bore (254) configured to matingly receive threading (256) of threaded member (250). With piston (220) in the proximal position, friction between threaded member (250) and sleeve (252) is sufficient to maintain engagement between threaded member (250) and sleeve (252) such that rotation of threaded member (250) will cause concurrent rotation of sleeve (252). A spring (256) positioned about threaded member (250) and between gear (251) and sleeve (252) is configured to increase friction between threaded member (250) and sleeve (252) by driving the threading of threaded bore (254) distally against the threading of threaded member (250). As discussed above, drive rod (28) is operable to rotate to thereby cause rotation of needle applier cartridge (30). It should therefore be understood that with piston (220) in the proximal position (FIG. 14), motor (202) is operable to selectively drive rotation of needle applier cartridge (30).

Figure 19:
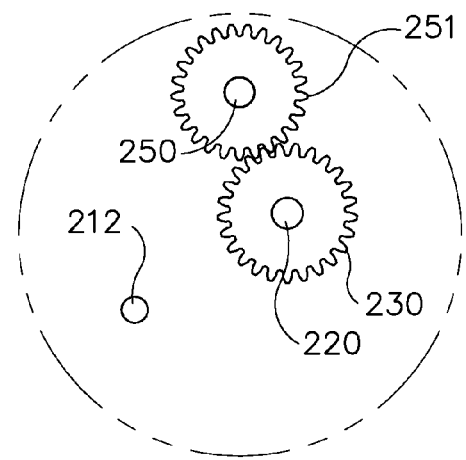
FIG. 19 depicts a cross-sectional view of drive components of the handle assembly of FIG. 15A, taken along line 19-19 of FIG. 15A.

As shown in FIGS. 15A-15B and 19, with piston (220) moved into the intermediate position, the teeth of gear (251) of threaded member (250) remain engaged with the teeth of gear (230) of piston (220) such that rotation of piston (220) causes concurrent rotation of threaded member (250). Piston (220) further includes a pawl (239) positioned between gears (230, 232). Pawl (239) is rotatably supported on piston (220) such that pawl (239) will translate longitudinally with piston (220) but not rotate with piston (220). By way of example only, pawl (239) may be secured to piston (220) by a bushing. Handle assembly (200) also includes boss features (not shown) that permit pawl (239) to translate within handle assembly (200) but prevent pawl (239) from rotating within handle assembly (200). With piston (220) in the proximal position, pawl (239) is disengaged from sleeve (252) such that sleeve (252) may freely rotate with threaded member (250).

As shown in FIG. 15A, however, with piston (220) moved into the intermediate position, pawl (239) is configured to engage the splines of spline feature (253) of sleeve (252) so as to prevent rotation of sleeve (252). Thus, with piston (220) in the intermediate position and with sleeve (252) prevented from rotating, rotation of threaded member (250) will cause translation of sleeve (252) due to the threaded engagement between threading (256) and threaded bore (254). As discussed above, drive rod (28) is operable to translate to thereby cause actuation of needle applier cartridge (30). It should therefore be understood that with piston (220) in the intermediate position (FIGS. 15A and 15B), motor (202) is operable to selectively actuate needle applier cartridge (30). As shown in FIG. 15B, as sleeve (252) translates distally, spline feature (253) simultaneously disengages pawl (239) of piston (220) and engages a flange (209) of handle assembly (200). Flange (209) is also configured to prevent rotation of sleeve (252) when flange (209) is engaged with spline feature (253). It should therefore be appreciated that pawl (239) and flange (209) cooperate to prevent rotation of sleeve (252) as sleeve (252) translates relative to handle assembly (200) through the range of motion shown in FIGS. 15A-15B to actuate needle applier cartridge (30).

Motor (202) and solenoid (204) are in communication with a plurality of operator inputs (280, 282, 284) and a power source (not shown) via a circuit board (290). Operator inputs (280, 282, 284) are positioned just like inputs (12, 14, 16) and provide an outward appearance that is similar to that of inputs (12, 14, 16). Operator input (280) includes a manually actuated trigger (e.g., similar to first input (12), etc.) that is operable to selectively activate a switch feature (292). Switch feature (292) is in communication with circuit board (290). The circuitry of circuit board (290) is configured such that activation of switch feature (292) will de-activate solenoid (204) to allow springs (225, 227) to drive piston (220) into the intermediate position (FIGS. 15A-15B); and then activate motor (202). It should therefore be understood that operator input (280) is operable to selectively actuate needle applier cartridge (30). It should also be understood that operator input (280) and switch feature (292) are just merely illustrative examples of features that may be used to actuate needle applier cartridge (30) via motor (202). Other suitable features that may be used in addition to or in lieu of operator input (280) and switch feature (292) will be apparent to those of ordinary skill in the art in view of the teachings herein.

Operator input (282) includes a rotary wheel that is operable to selectively activate a variable resistor feature (294). Variable resistor feature (294) is in communication with circuit board (290). The circuitry of circuit board (290) is configured such that activation of variable resistor feature (294) will consecutively actuate solenoid (204) so as to drive piston (220) into the distal position (FIG. 13); and then activate motor (202). It should therefore be understood that operator input (282) is operable to selectively articulate joint (23). It should also be understood that operator input (282) and variable resistor feature (294) are just merely illustrative examples of features that may be used to selectively articulate joint (23) via motor (202). Other suitable features that may be used in addition to or in lieu of operator input (282) and variable resistor feature (294) will be apparent to those of ordinary skill in the art in view of the teachings herein.

Operator input (284) also includes a rotary wheel that is operable to selectively activate a variable resistor feature (296). Variable resistor feature (296) is in communication with circuit board (290). The circuitry of circuit board (290) is configured such that activation of variable resistor feature (296) will consecutively actuate solenoid (204) so as to drive piston (220) into the proximal position (FIG. 14); and then activate motor (202). It should therefore be understood that operator input (284) is operable to selectively rotate needle applier cartridge (30). It should also be understood that operator input (284) and variable resistor feature (296) are just merely illustrative examples of features that may be used to selectively rotate needle applier cartridge (30) via motor (202). Other suitable features that may be used in addition to or in lieu of operator input (284) and variable resistor feature (296) will be apparent to those of ordinary skill in the art in view of the teachings herein.

In some versions, operator inputs (280, 282, 284) may include a foot actuated pedal in communication with solenoid (204) and/or motor (202). Other suitable forms that operator inputs (280, 282, 284) may take will be apparent to those of ordinary skill in the art in view of the teachings herein. It will also be understood that operator inputs (280, 282, 284) may be placed in any appropriate position on or relative to instrument (2) as will be apparent to one of ordinary skill in the art in view of the teachings herein. For instance, operator inputs (280, 282, 284) may be positioned on any portion of handle assembly (200). Alternatively, operator inputs (280, 282, 284) may also be positioned somewhere separately from instrument (2), which may include locating operator inputs (280, 282, 284) on a separate console or computer. Operator inputs (280, 282, 284) could also be located on a console or device in wireless communication with instrument (2). Other suitable locations for operator inputs (280, 282, 284) will be apparent to those of ordinary skill in the art in view of the teachings herein.

B. Exemplary Battery Packs

Figure 20B:
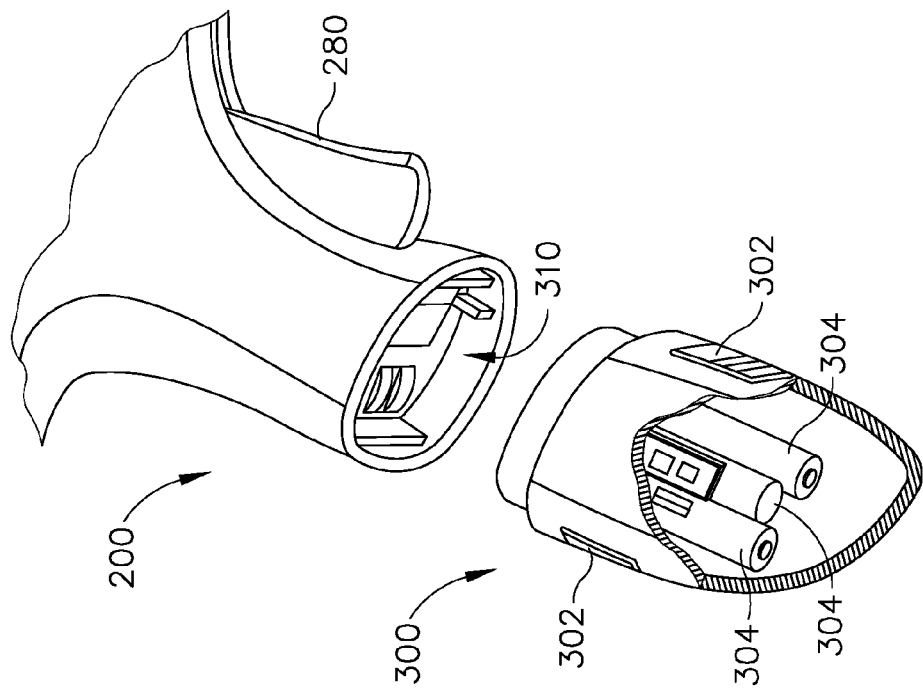
FIG. 20B depicts a partial view of the pistol grip of FIG. 20A, with a battery pack removed from a body of the handle assembly.
Figure 20A:
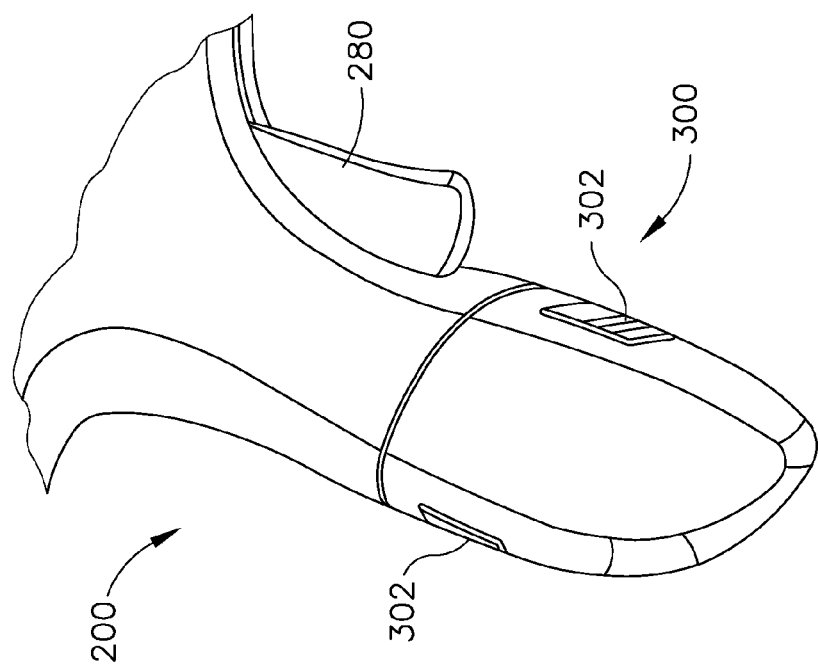
FIG. 20A depicts a partial view of a pistol grip of the handle assembly of FIG. 12.
Figure 21:
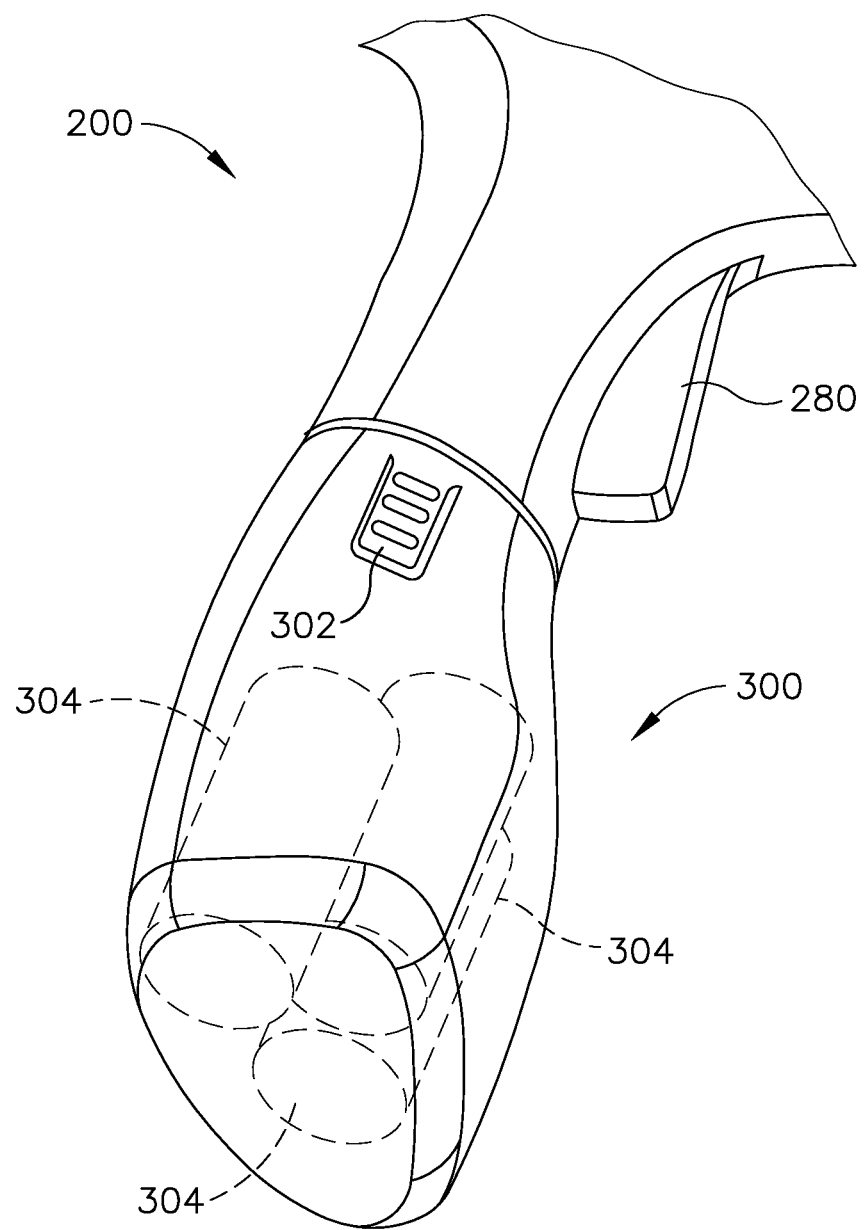
FIG. 21 depicts a partial view of a pistol grip of the handle assembly of FIG. 12 incorporating a larger battery pack.

As shown in FIGS. 20A, 20B, and 21, handle assembly (200) of the present example may further include a battery pack (300). Battery pack (300) is operable to provide electrical power to a motor (202) and solenoid (204). Battery pack (300) is removable from handle assembly (200). In particular, as shown in FIGS. 20A and 20B, battery pack (300) may be inserted into a socket (310) formed in handle assembly (200). Once battery pack (300) is fully inserted in socket (310), latches (302) of battery pack (300) may resiliently engage interior features of handle assembly (200) to provide a snap fit. To remove battery pack (300), the operator may press latches (302) inwardly to disengage latches (302) from the interior features of handle assembly (200) then pull battery pack (300) from socket (310). It should be understood that battery pack (300) and handle assembly (200) may have complementary electrical contacts, pins and sockets, and/or other features that provide paths for electrical communication from battery pack (300) to electrically powered components in handle assembly (200) when battery pack (300) is inserted in socket (310). It should also be understood that, in some versions, battery pack (300) is unitarily incorporated within handle assembly (200) such that battery back (300) cannot be removed from handle assembly (200). As shown between FIGS. 20A, 20B, and 21, different size batteries (304) may be included with battery pack (300) depending upon an operator's requirements/intended use. For instance, the larger battery pack (300) shown in FIG. 21 may provide greater power and/or a longer duration of use.

III. Exemplary Modular Shaft Assembly

In some instances, it may be desirable to replace the entire shaft (20) during or after performance of a surgical procedure. Such a replaceable shaft may include an integrated needle applier cartridge such that an operator need only replace the shaft instead of replacing the needle applier cartridge (30) as described above. Alternatively, such a replaceable shaft may removably receive a needle applier cartridge (30) as described above. Such a replaceable shaft may be used in conjunction with a manually driven handle assembly (10) as described above (see infra Part I) or in conjunction with a motorized handle assembly (200) as described above (see infra Part II). It may be desirable to provide such a replaceable shaft so as to provide a disposable/reusable dichotomy. For instance, the replaceable shaft may be provided as a disposable component while the handle assembly may be sterilized, reprocessed, reused, etc. Various examples of such replaceable shafts will be described in greater detail below; while other examples will be apparent to those of ordinary skill in the art according to the teachings herein.

A. Exemplary Modular Shaft Assembly with Coupling Along a Transverse Path

FIGS. 22-27 illustrate an exemplary alternative surgical suturing instrument (400). Instrument (400) comprises a handle assembly (410) and an elongate shaft (420). Shaft (420) has a proximal end (421), a distal end (422), and a longitudinal axis extending therebetween. As will be described in more detail below, handle assembly (410) is selectively coupleable to the proximal end (421) of the shaft (420). In this example handle assembly (410) is a manual pistol grip handle similar to handle assembly (10). However, a variety of other manual actuators could also be used, including but not limited to a scissor grip handle, a syringe grip handle, endoscopic rotary knobs, and the like. Handle assembly (410) could also take the form of a robotic interface, such as a DAVINCI puck, or a housing comprising gears or pulleys, servomechanisms, and the like. It should also be understood that handle assembly (410) may have motorized actuation features just like handle assembly (200).

Shaft (420) includes an integral cartridge receiving assembly (450) that is configured to receive and actuate a needle applier cartridge (30) in the same fashion as cartridge receiving assembly (50) described above. Cartridge receiving assembly (450) is positioned at the distal end (422) of shaft (420). Cartridge receiving assembly (450) is operable actuate a needle applier cartridge (30) to rotate an arced needle in a circular path enabling a surgeon to selectively apply sutures. In some alternative versions, needle applier cartridge (30) may be provided as a unitary, integral feature of shaft (420) such that the components of needle applier cartridge (30) may be integrally combined with components of cartridge receiving assembly (450). Distal end (422) of shaft (420) further comprises an articulation joint (423).

A first input (412), shown here as a trigger that pivots between opened and closed positions, may be used to selectively actuate a needle applier cartridge (30) via cartridge receiving assembly (450). The trigger may be spring biased to return the trigger to its open position. A second input (414), shown here as a rotary knob, may be used to selectively articulate cartridge receiving assembly (450) at articulation joint (423). A third input (416), shown here as a rotary knob, may be used to selectively rotate cartridge receiving assembly (450) and an associated cartridge (30) about the longitudinal axis of shaft (420). Of course, the number, type, configuration, and operation of inputs (412, 414, 416) may vary.

Figure 22:
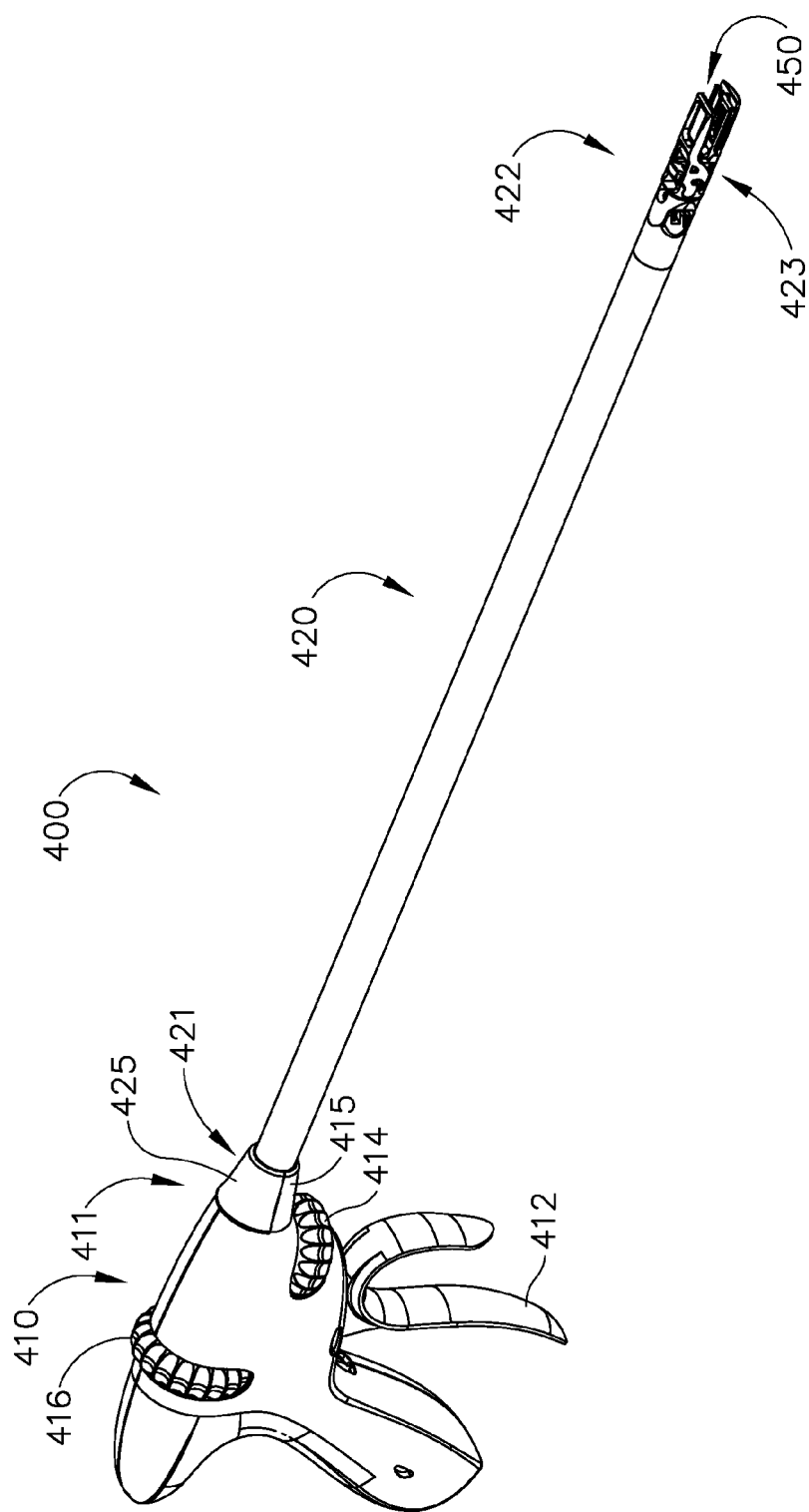
FIG. 22 depicts a perspective view of an exemplary alternative surgical suturing instrument.
Figure 23:
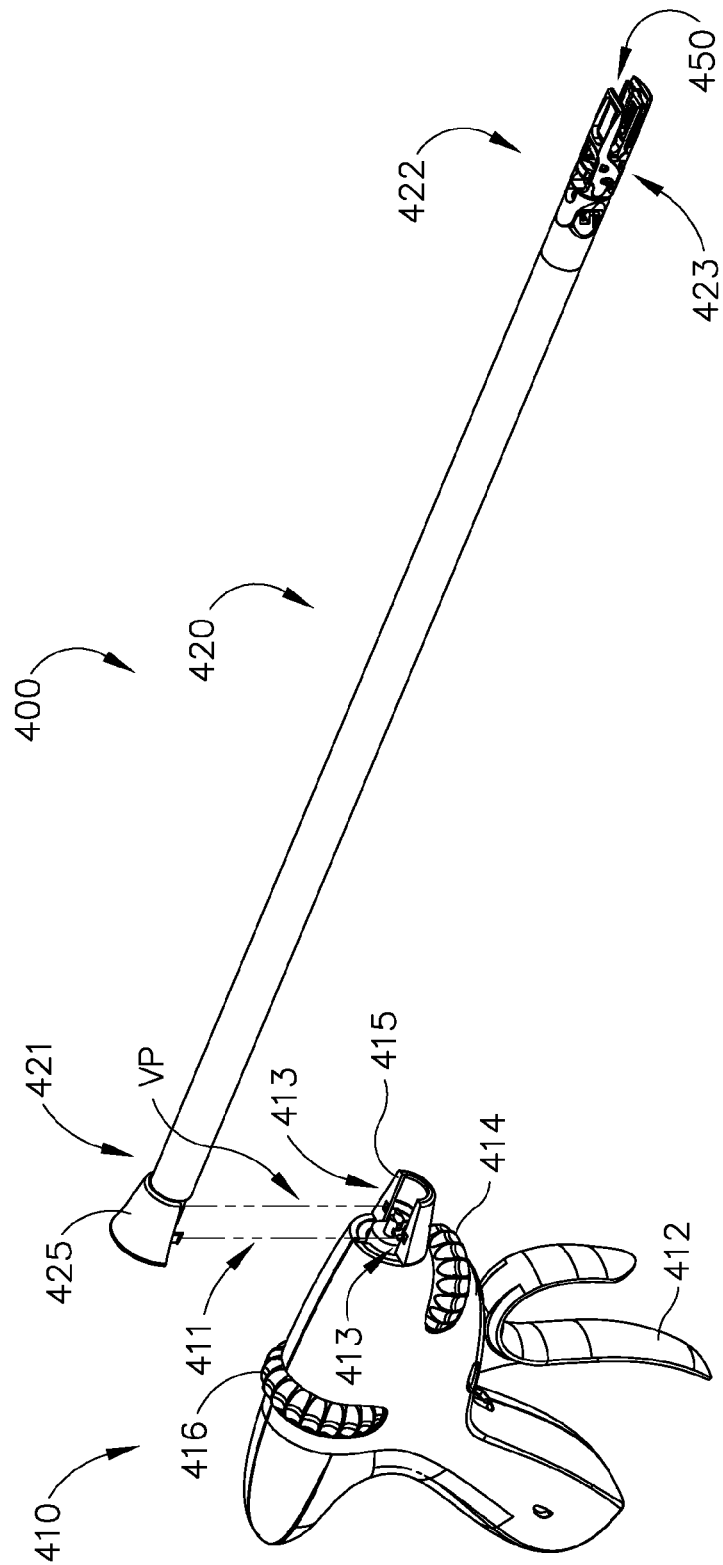
FIG. 23 depicts a perspective view of the instrument of FIG. 22, with a shaft assembly removed from the handle assembly.
Figure 24:
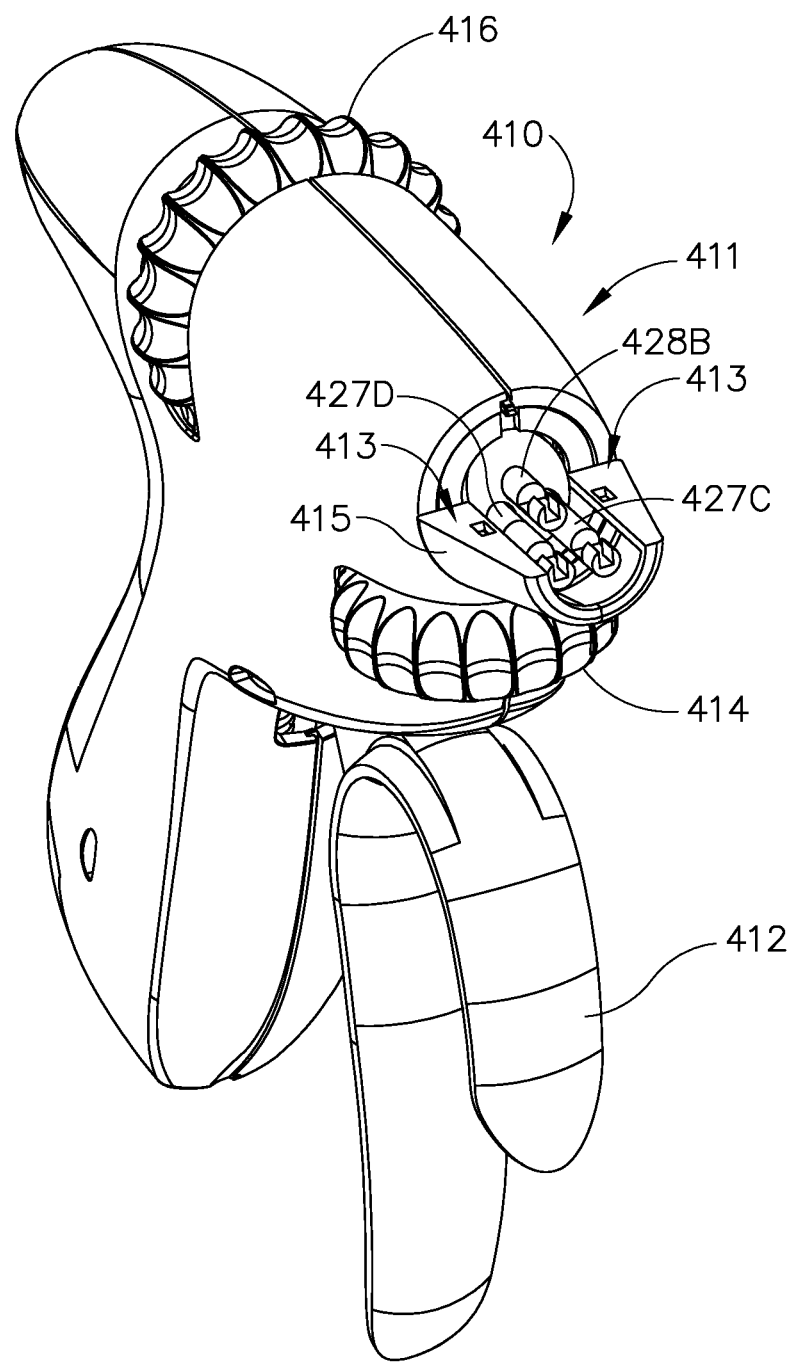
FIG. 24 depicts a perspective view of the handle assembly of FIG. 23.
Figure 25:
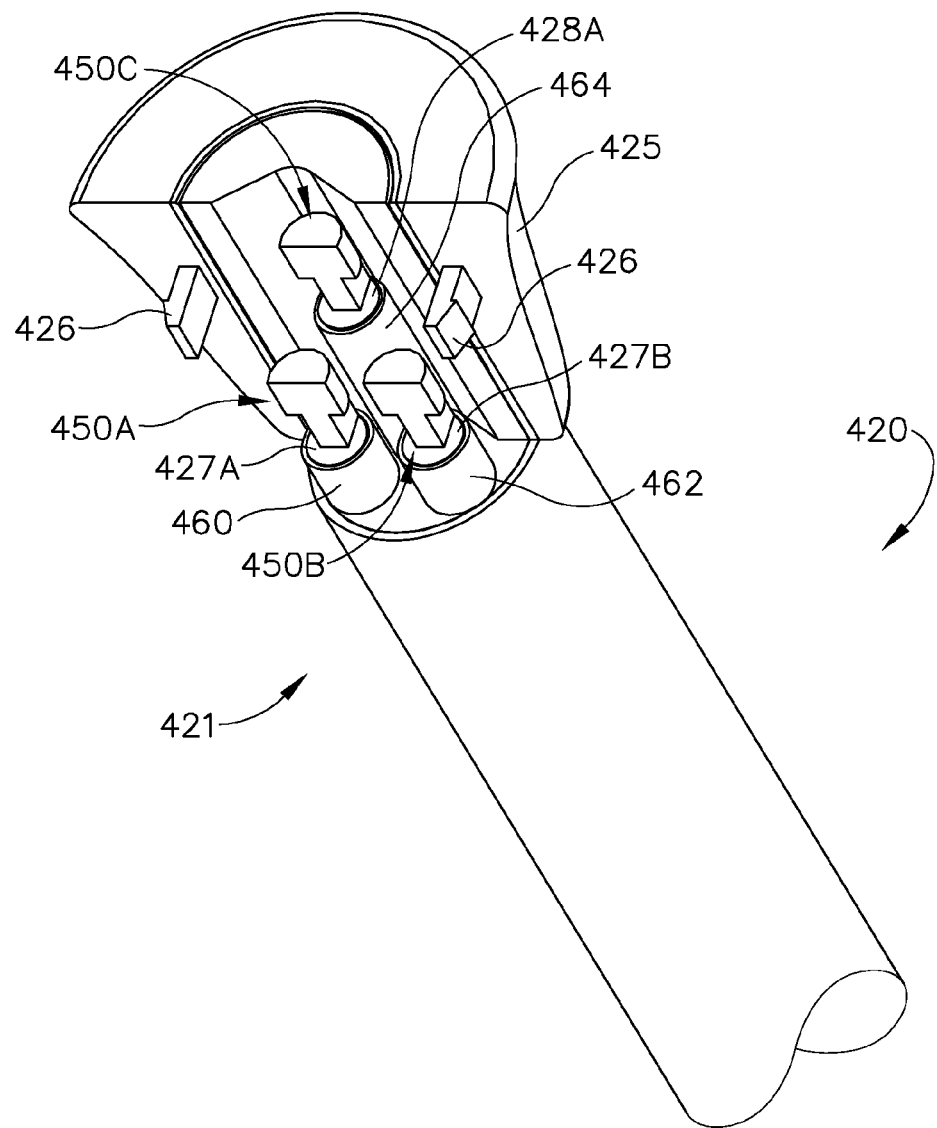
FIG. 25 depicts a perspective view of a proximal end of the shaft assembly of FIG. 23.

As shown in FIG. 23, shaft (420) is removable from handle assembly (410). As best seen in FIG. 24, a distal end (411) of handle assembly (410) includes a semi-conical hub (415). As best seen in FIG. 25, proximal end (421) of shaft (420) includes a mating semi-conical hub (425). As will be described in detail below, shaft (420) is guided along a vertical path (VP) (that is transverse to the longitudinal axis of shaft (420)) toward hub (415) to thereby couple shaft (420) with handle assembly (410). As shown in FIG. 22, with shaft (420) coupled with handle assembly (410), hubs (415, 425) are configured to align with one another to form a substantially continuous conical hub. Once shaft (420) is coupled with handle assembly (410), a pair of latches (426) of hub (425) may resiliently engage a pair of sockets (413) formed in hub (415) to provide a snap fit between shaft (420) and handle assembly (410). To remove shaft (420) from handle assembly (410), the operator may disengage latches (426) of hub (425) from sockets (413) of hub (415) then remove shaft (420) from handle assembly (410) along the same vertical path (VP) used to couple shaft (420) with handle assembly (410).

Figure 26:
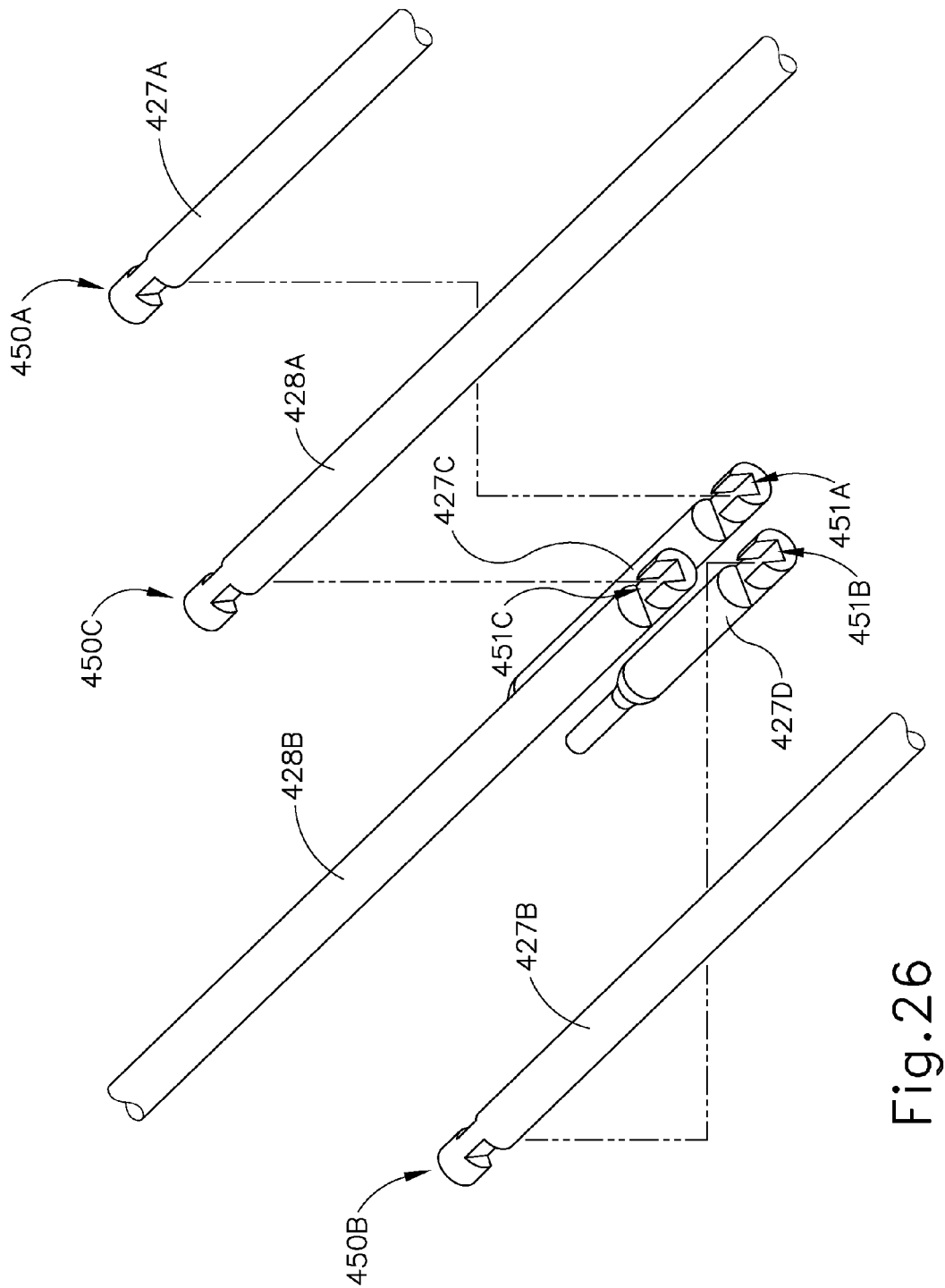
FIG. 26 depicts an exploded view of actuation shafts of the instrument of FIG. 22.
Figure 27:
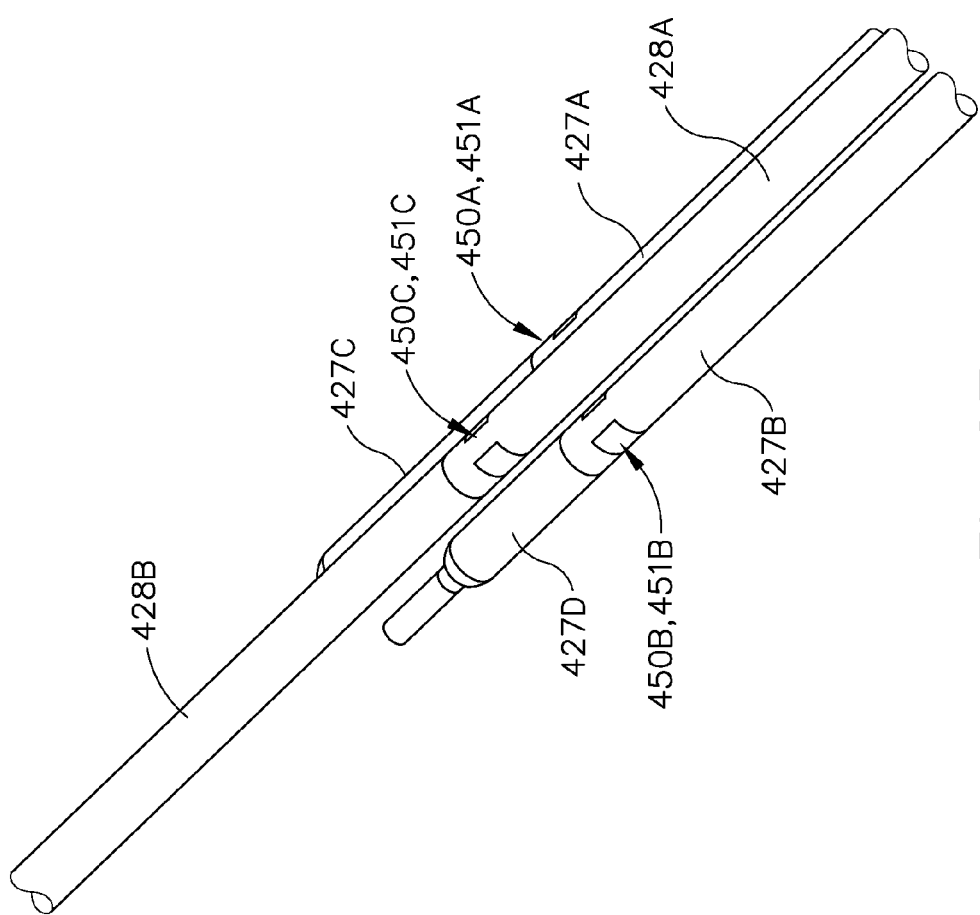
FIG. 27 depicts a perspective view of the actuation shafts of FIG. 26 joined together.
Figure 28:
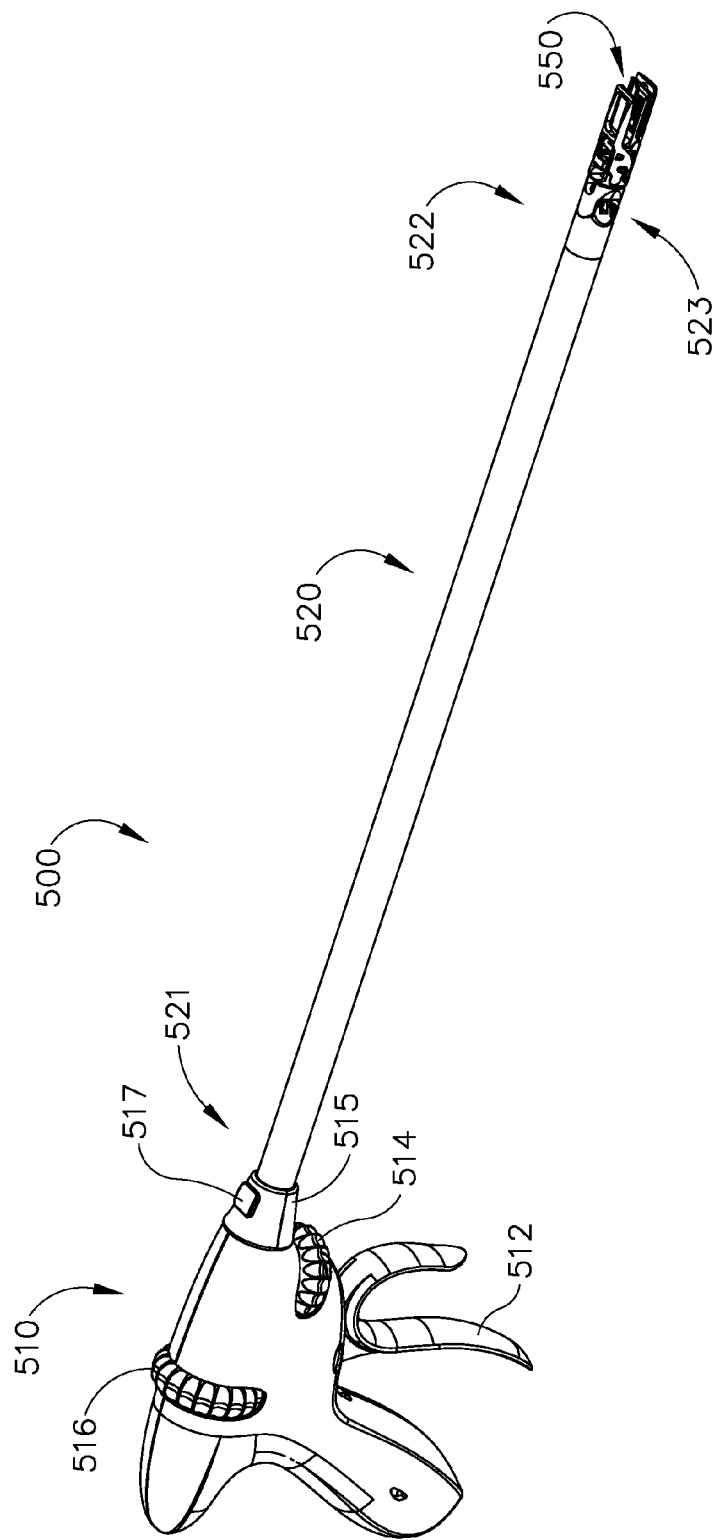
FIG. 28 depicts a perspective view of another exemplary alternative surgical suturing instrument.

A pair of articulation rods (427A, 427B) are operatively connected to articulation joint (423). Rods (427A, 427B) are shown in FIGS. 25-27. In this example, rods (427A, 427B) are slidably disposed within shaft (420) such that rods (427A, 427B) are configured to translate longitudinally within and relative to shaft (420). Proximal ends of rods (427A, 427B) extend from proximal end (421) of shaft (420). A pair of mating articulation rods (427C, 427D) extends through handle assembly (410) such that a distal end of each rod (427C, 427D) extends from a distal end of handle assembly (410). Rods (427C, 427D) are operatively connected to rotary knob (414) to opposingly push and pull rods (427C, 427D). In other words, rotary knob (414) is operable to drive rods (427C, 427D) at the same time in opposite longitudinal directions, such that rod (427C) will translate distally while rod (427D) translates proximally; and such that rod (427C) will translate distally while rod (427D) translates proximally. As will be described in more detail below, rods (427A, 427B) of shaft (420) are configured to couple respectively with rods (427C, 427D) of handle assembly (410) such that rod (427A) will translate concurrently with rod (427C) and such that rod (427B) will translate concurrently with rod (427D). Accordingly, rods (427A, 427B, 427C, 427D) operate to articulate shaft (420) in the same fashion in which rods (27A, 27B) articulate shaft (20) as described above.

A drive rod (428A) is slidably disposed within shaft (420) such that drive rod (428A) is configured to translate longitudinally within and relative to shaft (420). A proximal end of rod (428A) extends from proximal end (421) of shaft (420). A mating drive rod (428B) extends through handle assembly (410) such that a distal end of drive rod (428B) extends from the distal end of handle assembly (410). Drive rod (428B) is operatively connected to first input (412) and to third input (416). Actuation of first input (412) will impart axial push and pull loads on drive rod (428B) to thereby actuate a needle applier cartridge (30) as described above with reference to instrument (2) via cartridge receiving assembly (450). Actuation of third input (416) will impart a rotational load on drive rod (428B) thus rotating needle applier cartridge (30) relative to shaft (420) as described above with reference to instrument (2) via cartridge receiving assembly (450). As will be described in more detail below, drive rod (428A) of shaft (420) is configured to couple with drive rod (428B) of handle assembly (410) such that drive rod (428A) will translate and rotate concurrently with drive rod (428B). Accordingly, drive rods (428A, 428B) operate to both actuate a needle applier cartridge (30) via cartridge receiving assembly (450) as well as control distal rotation of cartridge receiving assembly (450) about the longitudinal axis of shaft (420). By consolidating dual functions within drive rods (428A, 428B), the number of components is reduced, and more space is provided in the shaft (420), which may make instrument (400) less expensive to manufacture and easier to clean.

As best seen in FIGS. 26-27, the proximal ends of rods (427A, 427B, 428A) of shaft (420) include T-shaped projections (450A, 450B, 450C). The distal ends of rods (427C, 427D, 428B) of handle assembly (410) include T-shaped slots (451A, 451B, 451C) formed therein. Projections (450A, 450B, 450C) of rods (427A, 427B, 428A) are configured to mate with and engage slots (451A, 451B, 451C) of rods (427C, 427D, 428B). This engagement between projections (450A, 450B, 450C) and slots (451A, 451B, 451C) is configured to communicate translation and rotation of rods (427C, 427D, 428B) of handle assembly (410) to rods (427A, 427B, 428A) of shaft (420).

As best seen in FIG. 25, hub (425) includes a set of sleeves (460, 462, 464) through which rods (427A, 427B, 428A) extend. Sleeves (460, 462, 464) remain stationary relative to shaft (420) while rods (427A, 427B, 428A) are translatable within shaft (420). Sleeves (460, 462, 464) are configured to prevent mating of rods (427A, 427B, 428B) of shaft (420) with rods (427C, 427D, 428B) of handle assembly (410) unless rods (427A, 427B, 428A) are in a "home" position (i.e., a proximal position) relative to shaft (420). In other words, if any rod (427A, 427B, 428A) is positioned distal to the home position, the corresponding sleeve (460, 462, 464) will prevent T-shaped projection (450A, 450B, 450C) of the distally positioned rod (427A, 427B, 428A) from coupling with the complementary slot (451A, 451B, 451C) of the corresponding rod (427C, 427D, 428B).

In some versions of instrument (400), shaft (420) and/or handle assembly (410) may be provided as being disposable or reusable. Versions with reusable components are intended to be cleaned, sterilized, and reused for multiple surgical procedures, and may include a flush port (not shown) to facilitate cleaning. In some such versions, the preferable life cycle of a reusable instrument may be at least 50 operations, more particularly at least 150 operations, or more particularly at least 200 operations. Reusable components may be built using materials that can withstand autoclave sterilization temperatures of at least 135 degrees Celsius, although low temperature materials can also be used with low temperature sterilization techniques known in the art.

B. Exemplary Modular Shaft Assembly with Coupling Along a Longitudinal Path

FIGS. 28-40B illustrate another exemplary alternative surgical suturing instrument (500). Instrument (500) comprises a handle assembly (510) and an elongate shaft (520). Shaft (520) has a proximal end (521), a distal end (522), and a longitudinal axis extending therebetween. As will be described in more detail below, handle assembly (510) is selectively coupleable to the proximal end (521) of the shaft (520). In this example handle assembly (510) is a manual pistol grip handle. However, a variety of other manual actuators could also be used, including but not limited to a scissor grip handle, a syringe grip handle, endoscopic rotary knobs, and the like. Handle assembly (510) could also take the form of a robotic interface, such as a DAVINCI puck, or a housing comprising gears or pulleys, servomechanisms, and the like. It should also be understood that handle assembly (510) may have motorized actuation features just like handle assembly (200).

Shaft (520) includes an integral cartridge receiving assembly (550) that is configured to receive and actuate a needle applier cartridge (30) in the same fashion as cartridge receiving assembly (50) described above. Cartridge receiving assembly (550) is positioned at the distal end (522) of shaft (520). Cartridge receiving assembly (550) is operable actuate a needle applier cartridge (30) to rotate an arced needle in a circular path enabling a surgeon to selectively apply sutures. In some alternative versions, needle applier cartridge (30) may be provided as a unitary, integral feature of shaft (520) such that the components of needle applier cartridge (30) may be integrally combined with components of cartridge receiving assembly (550). Distal end (522) of shaft (520) further comprises an articulation joint (523).

A first input (512), shown here as a trigger that pivots between opened and closed positions, may be used to selectively actuate a needle applier cartridge (30) via cartridge receiving assembly (550). The trigger may be spring biased to return the trigger to its open position. A second input (514), shown here as a rotary knob, may be used to selectively articulate cartridge receiving assembly (550) at articulation joint (523). A third input (516), shown here as a rotary knob, may be used to selectively rotate cartridge receiving assembly (550) and an associated cartridge (30) about the longitudinal axis of shaft (520). Of course, the number, type, configuration, and operation of inputs (512, 514, 516) may vary.

Figure 29:
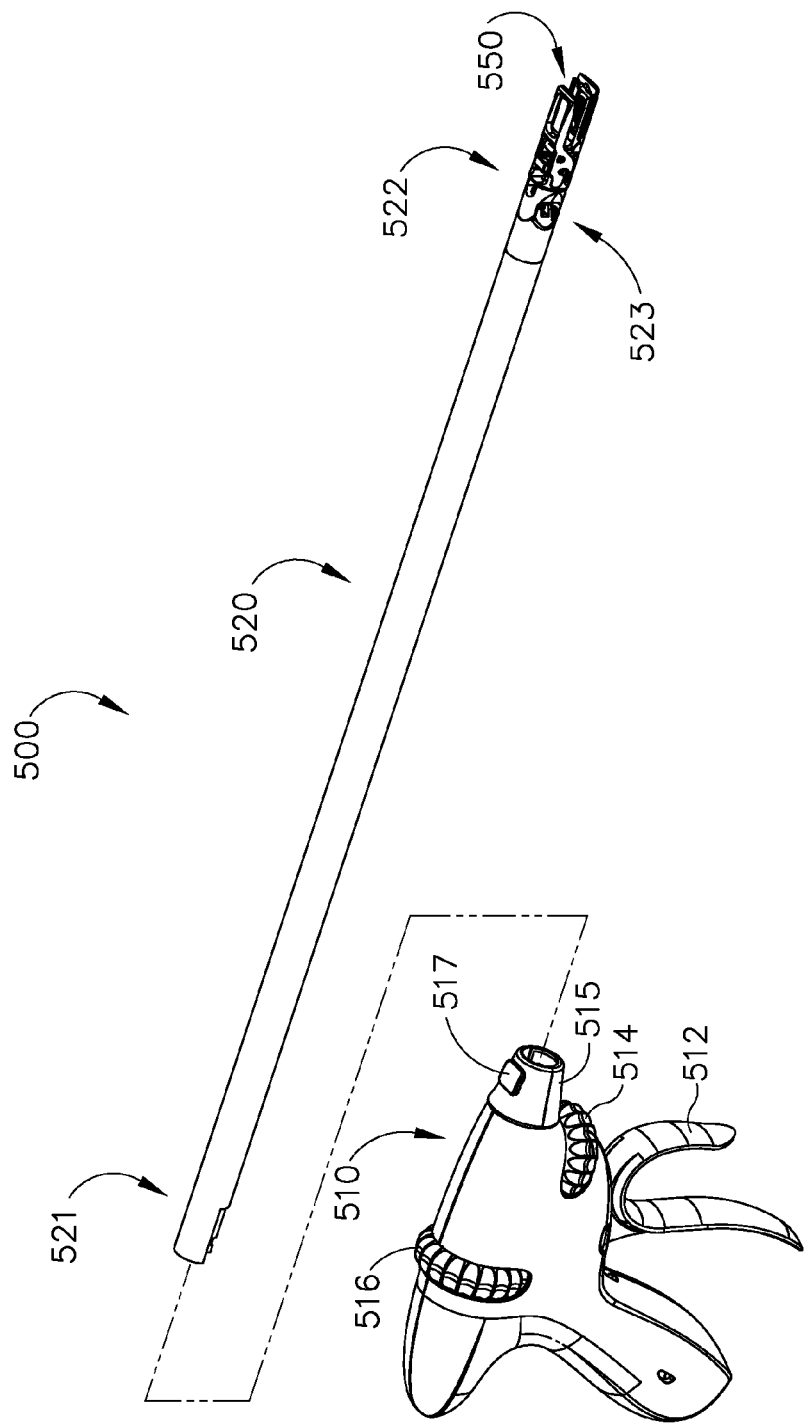
FIG. 29 depicts a perspective view of the instrument of FIG. 28, with a shaft assembly removed from the handle assembly.
Figure 30:
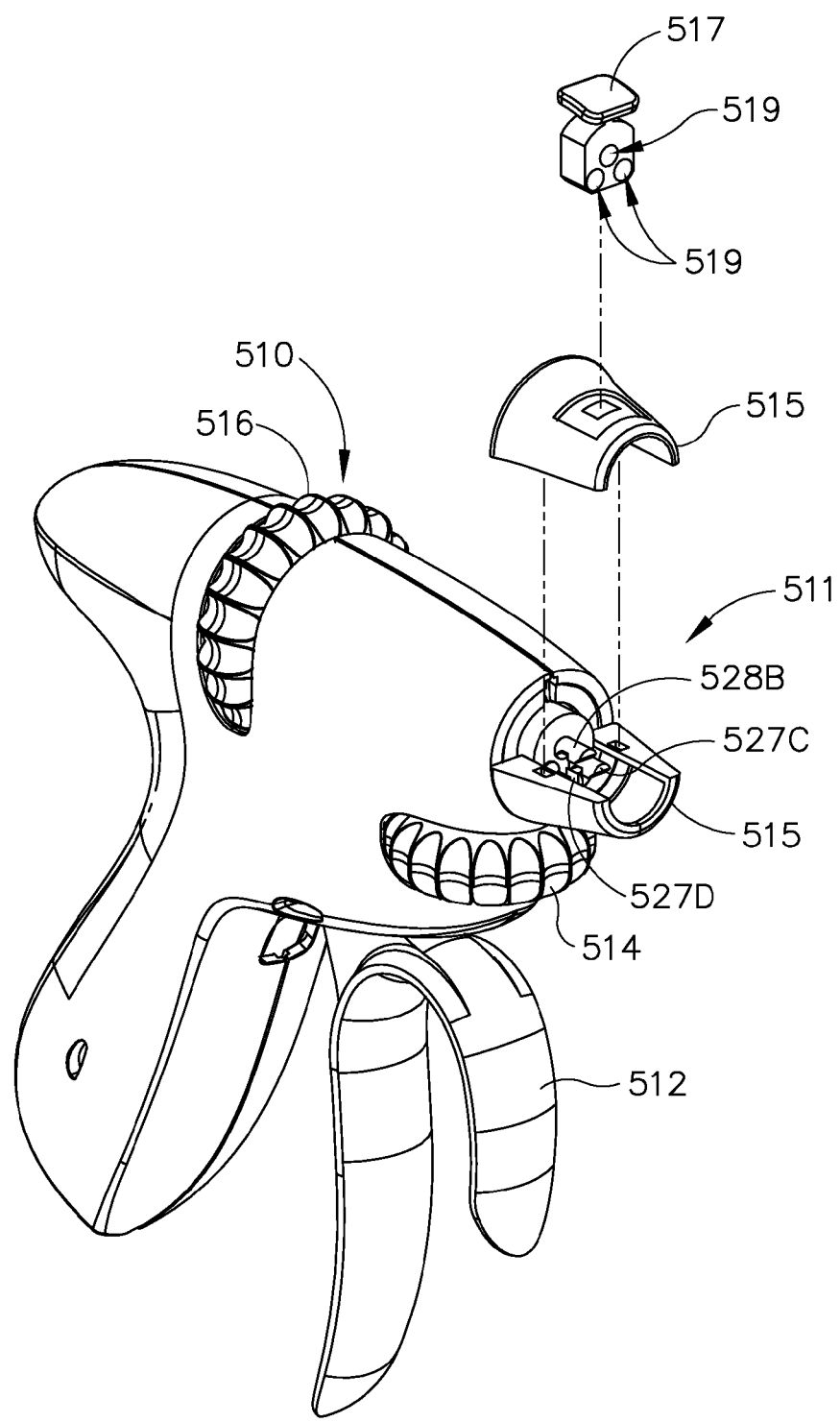
FIG. 30 depicts a perspective view of the handle assembly of FIG. 29.

As shown in FIG. 29, shaft (520) is removable from handle assembly (510). As best seen in FIG. 30, a distal end (511) of handle assembly (510) includes a conical hub (515). Hub (515) is configured to removably receive shaft (520) as will be described in more detail below. Hub (515) includes a button (517). Button (517) is slidably disposed within hub (515) such that button (517) is operable to translate vertically between a first position (FIG. 39C) and a second position (FIG. 39D). As will be described in more detail below, button (517) is operable to translate between the first position and the second position to disengage shaft (520) from handle assembly (510). Shaft (520) may be inserted into handle assembly (510) and removed from handle assembly (510) along a path that is coaxial with the longitudinal axis of shaft (520).

Figure 31:
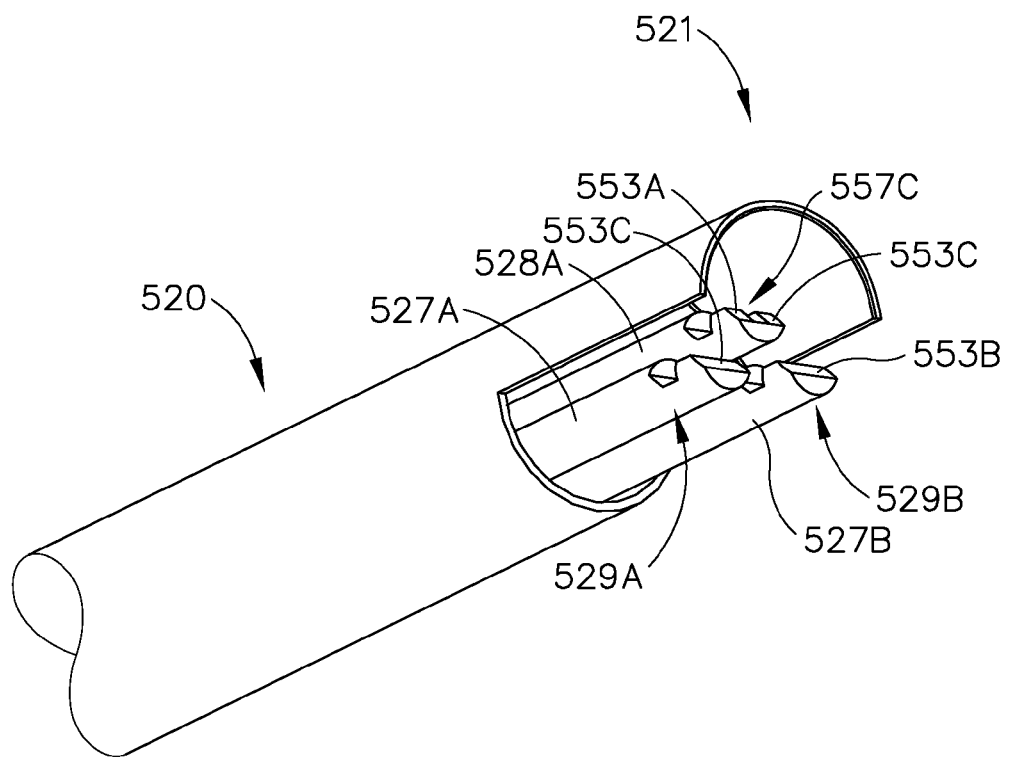
FIG. 31 depicts a perspective view of a proximal portion of the shaft assembly of FIG. 29.
Figure 32:
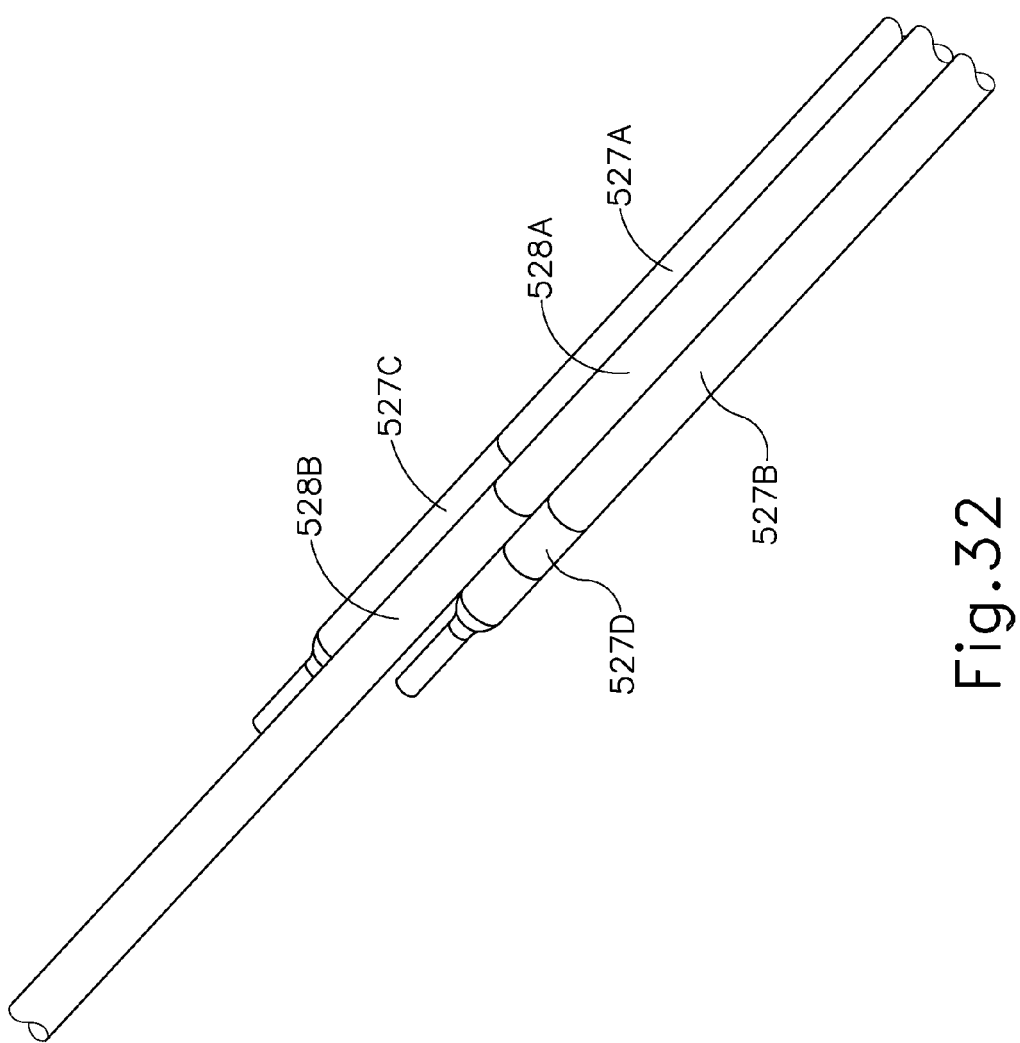
FIG. 32 depicts a perspective view of actuation shafts of the instrument of FIG. 28.
Figure 34:
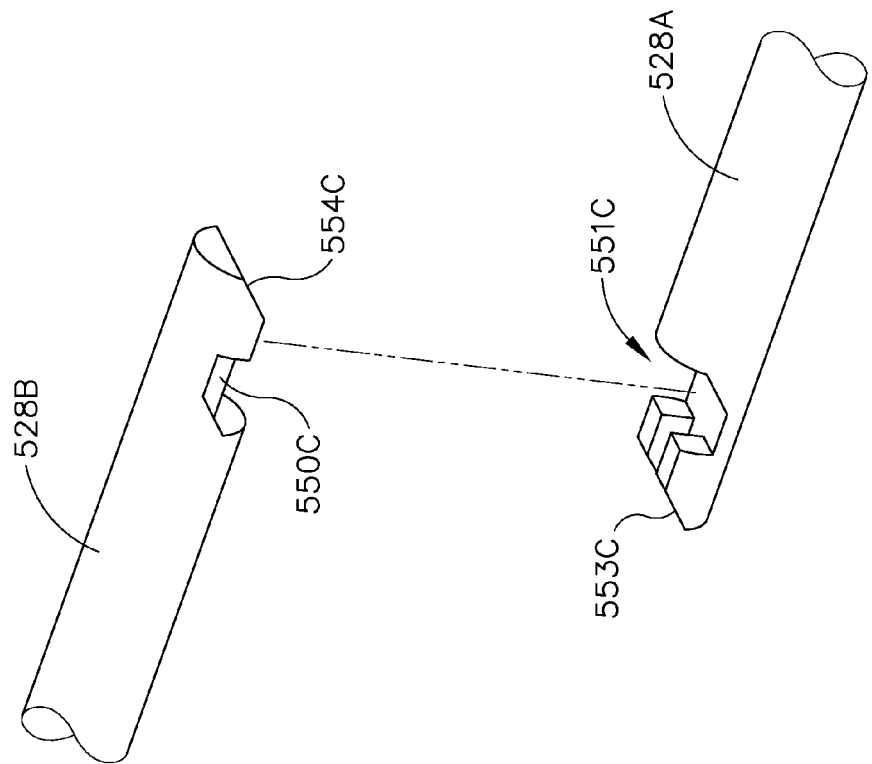
FIG. 34 depicts an exploded view of the head drive shafts of FIG. 33.
Figure 33:
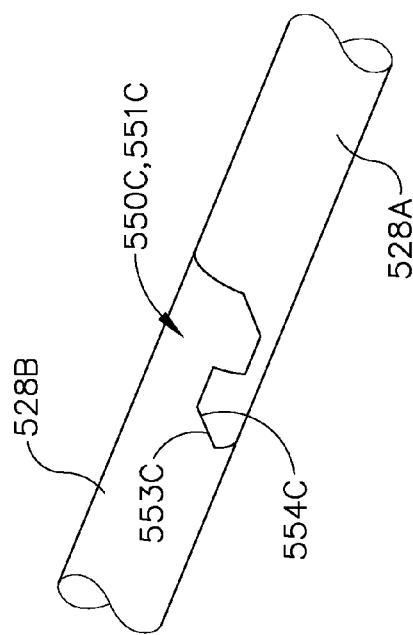
FIG. 33 depicts a perspective view of head drive shafts of the actuation shafts of FIG. 32.
Figure 35:
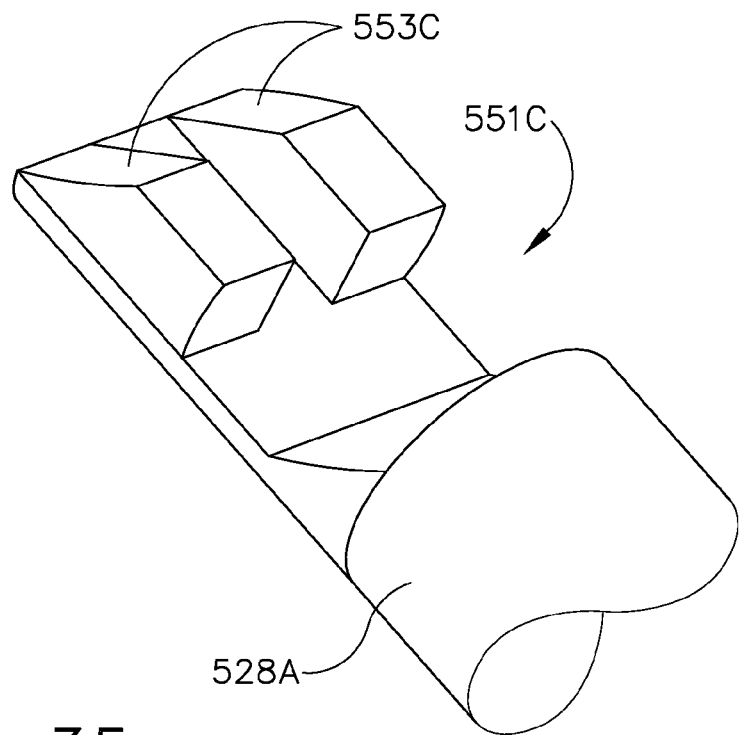
FIG. 35 depicts a perspective view of the proximal end of a distal head drive shaft of the head drive actuation shafts of FIG. 33.
Figure 36:
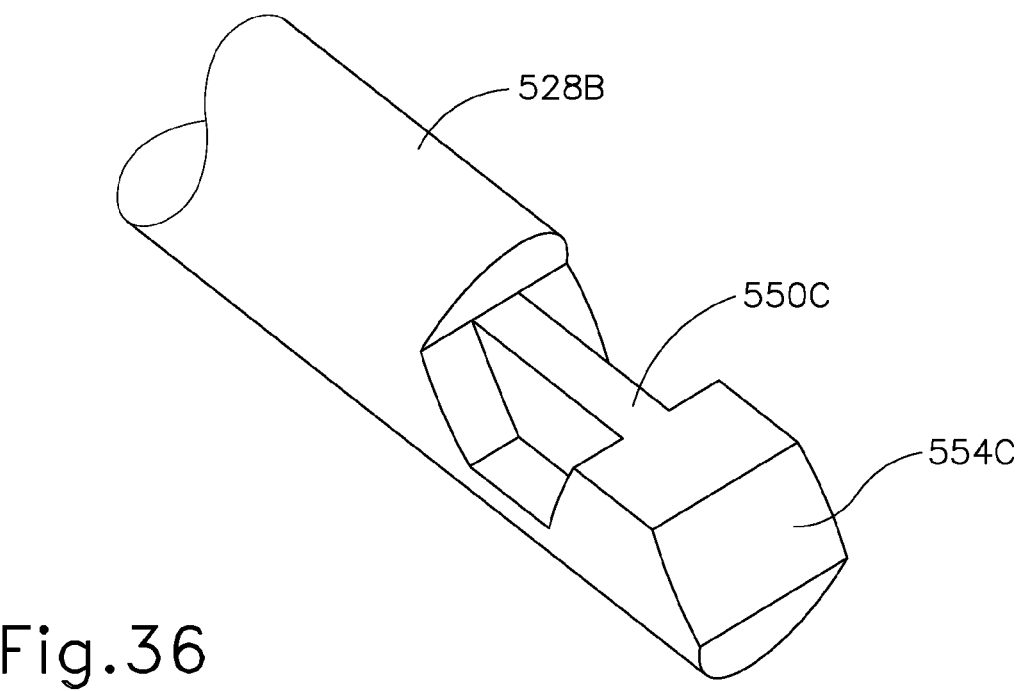
FIG. 36 depicts a perspective view of the distal end of a proximal head drive shaft of the head drive actuation shafts of FIG. 33.

A pair of articulation rods (527A, 527B) are operatively connected to articulation joint (523). Rods (527A, 527B) are shown in FIGS. 31-32. In this example, rods (527A, 527B) are slidably disposed within shaft (520) such that rods (527A, 527B) are configured to translate longitudinally within and relative to shaft (520). Proximal ends (529A, 529B) of rods (527A, 527B) extend from proximal end (521) of shaft (520) as best seen in FIG. 31. Rods (527A, 527B) are sufficiently flexible such that proximal ends (529A, 529B) of rods (527A, 527B) are operable to flex laterally relative to a longitudinal axis of shaft (520). A pair of mating articulation rods (527C, 527D) extends through handle assembly (510) such that a distal end of each rod (527C, 527D) extends from a distal end of handle assembly (510) as best seen in FIG. 30. Rods (527C, 527D) are operatively connected to rotary knob (514) to opposingly push and pull rods (527C, 527D). In other words, rotary knob (514) is operable to drive rods (527C, 527D) at the same time in opposite longitudinal directions, such that rod (527C) will translate distally while rod (527D) translates proximally; and such that rod (527C) will translate distally while rod (527D) translates proximally. As will be described in more detail below, rods (527A, 527B) of shaft (520) are configured to couple respectively with rods (527C, 527D) of handle assembly (510) such that rod (527A) will translate concurrently with rod (527C) and such that rod (527B) will translate concurrently with rod (527D). Accordingly, rods (527A, 527B, 527C, 527D) operate to articulate shaft (520) in the same fashion in which rods (27A, 27B) articulate shaft (20) as described above.

A drive rod (528A) is slidably disposed within shaft (520) such that drive rod (528A) is configured to translate longitudinally within and relative to shaft (520). A proximal end (529C) of rod (528A) extends from proximal end (521) of shaft (520). Drive rod (528A) is sufficiently flexible such that proximal end (529C) of drive rod (528A) is operable to flex laterally relative to a longitudinal axis of shaft (520). A mating drive rod (528B) extends through handle assembly (510) such that a distal end of drive rod (528B) extends from the distal end of handle assembly (510). Drive rod (528B) is operatively connected to first input (512) and to third input (516). Actuation of first input (512) will impart axial push and pull loads on drive rod (528B) to thereby actuate a needle applier cartridge (30) as described above with reference to instrument (2) via cartridge receiving assembly (550). Actuation of third input (516) will impart a rotational load on drive rod (528B) thus rotating needle applier cartridge (30) relative to shaft (520) as described above with reference to instrument (2) via cartridge receiving assembly (550). As will be described in more detail below, drive rod (528A) of shaft (520) is configured to couple with drive rod (528B) of handle assembly (510) such that drive rod (528A) will translate and rotate concurrently with drive rod (528B). Accordingly, drive rods (528A, 528B) operate to both actuate a needle applier cartridge (30) via cartridge receiving assembly (550) as well as control distal rotation of cartridge receiving assembly (550) about the longitudinal axis of shaft (520). By consolidating dual functions within drive rods (528A, 528B), the number of components is reduced, and more space is provided in the shaft (520), which may make instrument (500) less expensive to manufacture and easier to clean.

As best seen in FIGS. 33-36, proximal end (529C) of drive rod (528A) of shaft (520) includes a T-shaped slot (551C) formed therein. Proximal end (529C) of drive rod (528A) further includes an angled surface (553C). A distal end of drive rod (528B) of handle assembly (510) includes a T-shaped projection (550C). The distal end of drive rod (528B) further includes an angled surface (554C). Projection (550C) of drive rod (528B) is configured to mate with and engage slot (551C) of drive rod (528A). This engagement between projection (550C) and slot (551C) is configured to communicate translation and rotation of drive rod (528B) of handle assembly (510) to drive rod (528A) of shaft (520). As will be discussed in more detail below, surfaces (553C, 554C) are configured to engage one another as shaft (520) is inserted into hub (515) of handle assembly (510) so as to cause deflection of drive rod (528A).

Figure 37:
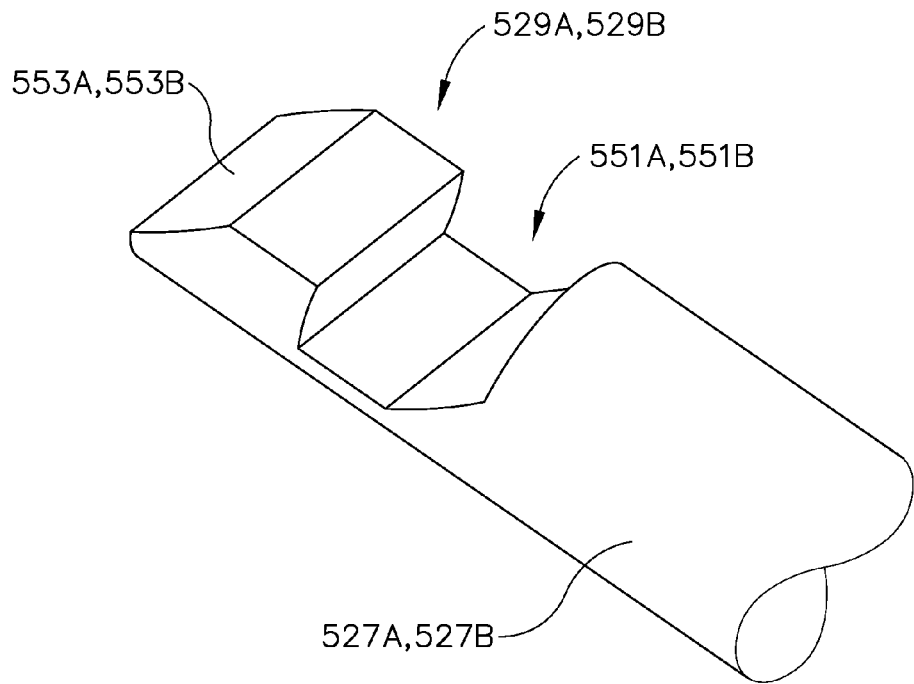
FIG. 37 depicts a perspective view of the proximal end of a distal articulation drive shaft of the actuation shafts of FIG. 32.
Figure 38:
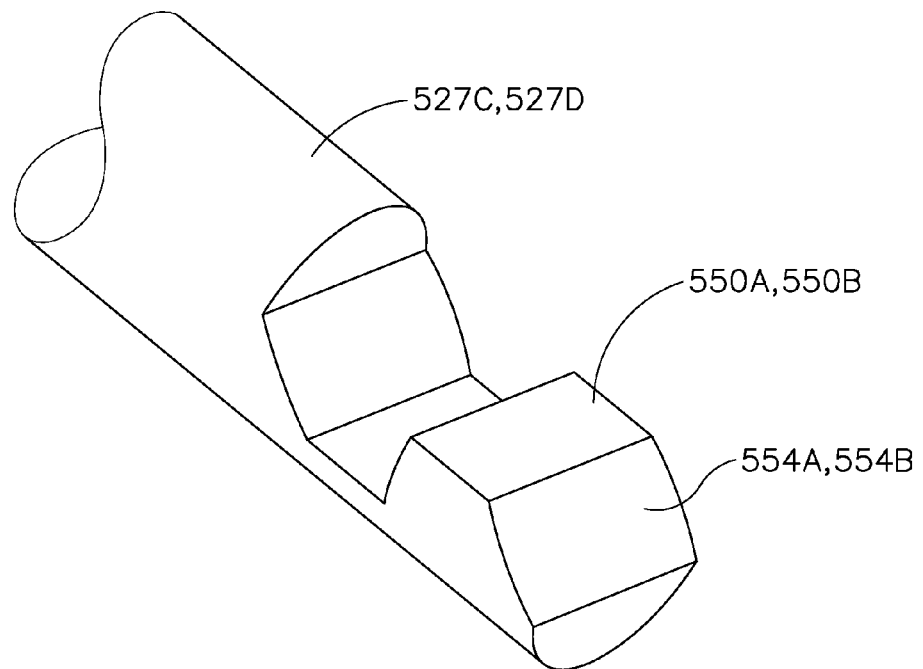
FIG. 38 depicts a perspective view of the distal end of a proximal articulation drive shaft of the actuation shafts of FIG. 32.

As best seen in FIGS. 37-38, proximal ends (529A, 529B) of rods (527A, 527B) of shaft (520) include transverse slots (551A, 551B) formed therein. Proximal end ends (529A, 529B) of rods (527A, 527B) further include angled surfaces (553A, 553B). Distal ends of rods (527C, 527D) of handle assembly (510) include transverse projections (550A, 550B). The distal ends of rods (527C, 527D) further include angled surfaces (554A, 554B). Projections (550A, 550B) of rods (527C, 527D) are configured to mate with and engage slots (551A, 551B) of rods (527A, 527B). This engagement between projections (550A, 550B) and slots (551A, 551B) is configured to communicate translation of rods (527C, 527D) of handle assembly (510) to rods (527A, 527B) of shaft (520). As will be discussed in more detail below, surfaces (553A, 553B, 554A, 554B) are configured to engage one another as shaft (520) is inserted into hub (515) of handle assembly (510) so as to cause deflection of rods (527A, 527B).

Figure 39A:
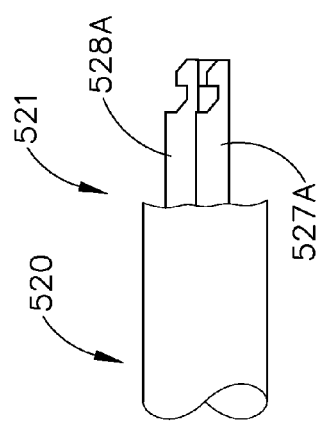
FIG. 39A depicts a partial side elevational view of the instrument of FIG. 28, with portions of the shaft and handle assemblies cut away to reveal internal components, with the shaft assembly separated from the handle assembly.
Figure 39A:
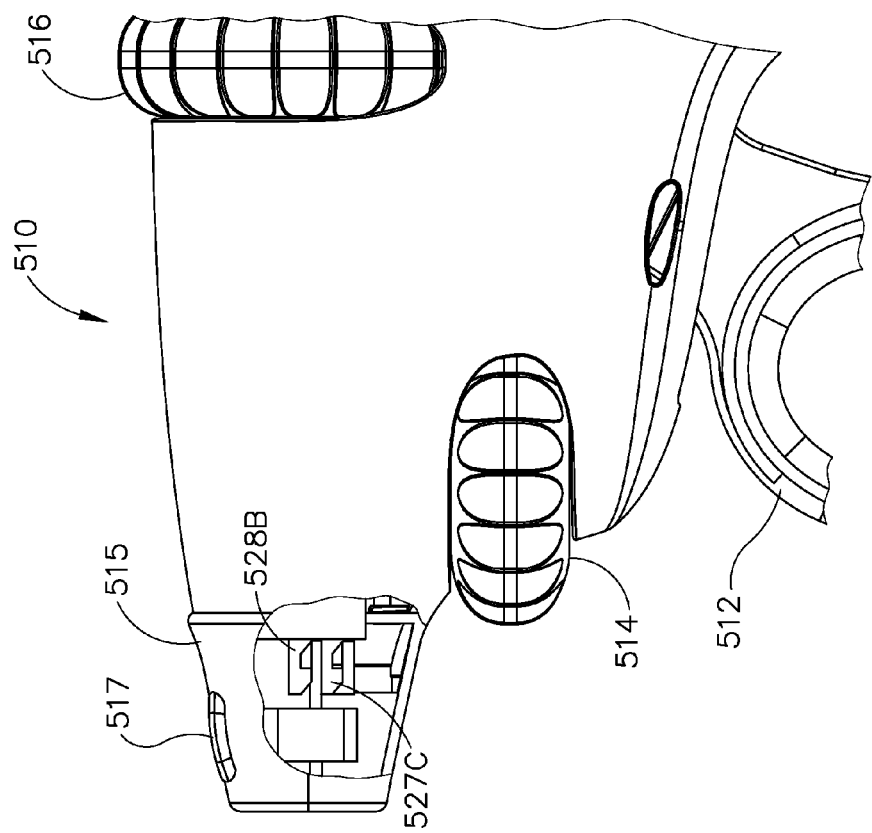
Figure 39B:
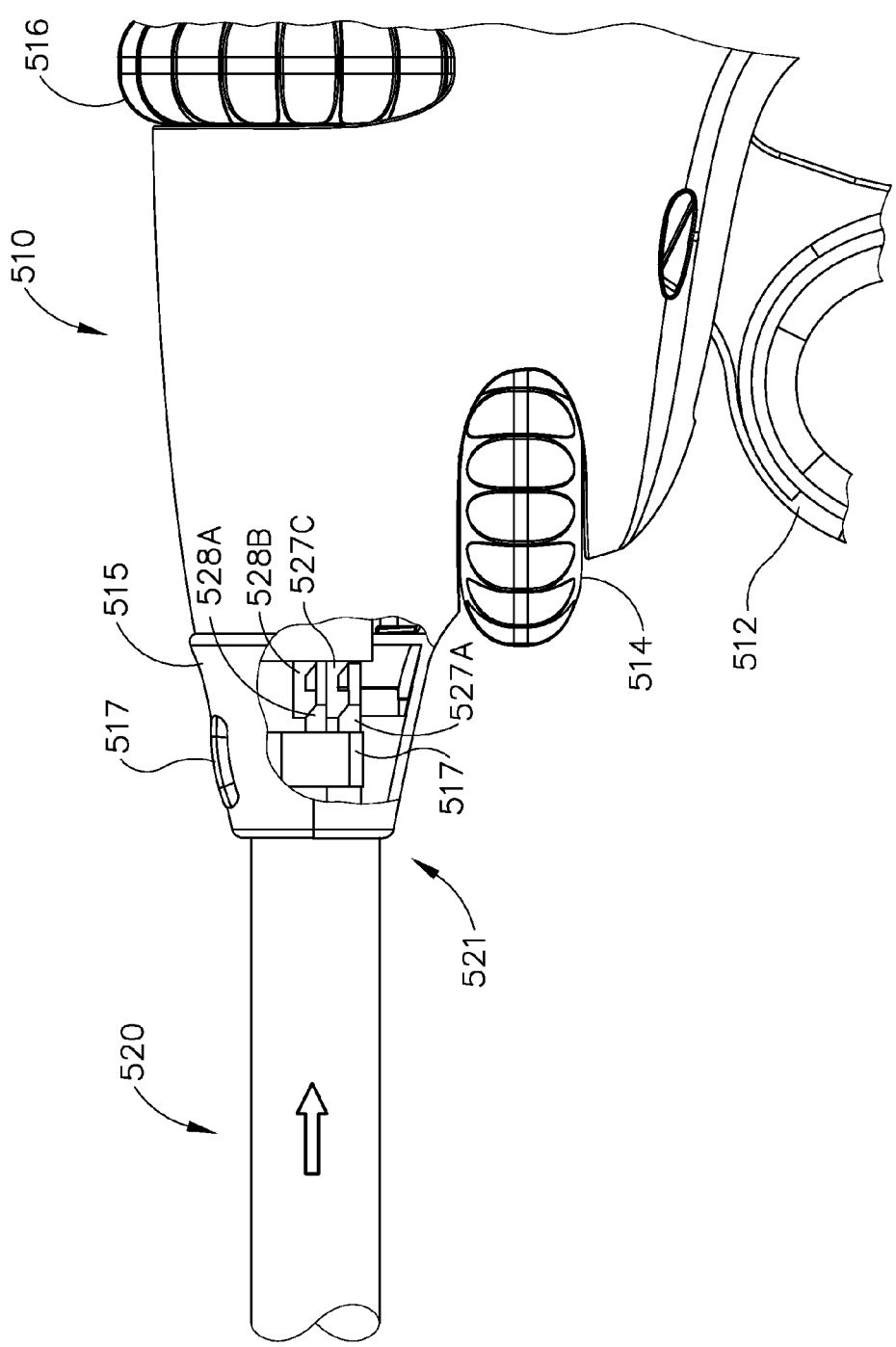
FIG. 39B depicts a partial side elevational view of the instrument of FIG. 28, with portions of the shaft and handle assemblies cut away to reveal internal components, with the shaft assembly at a first stage of insertion into the handle assembly.
Figure 39C:
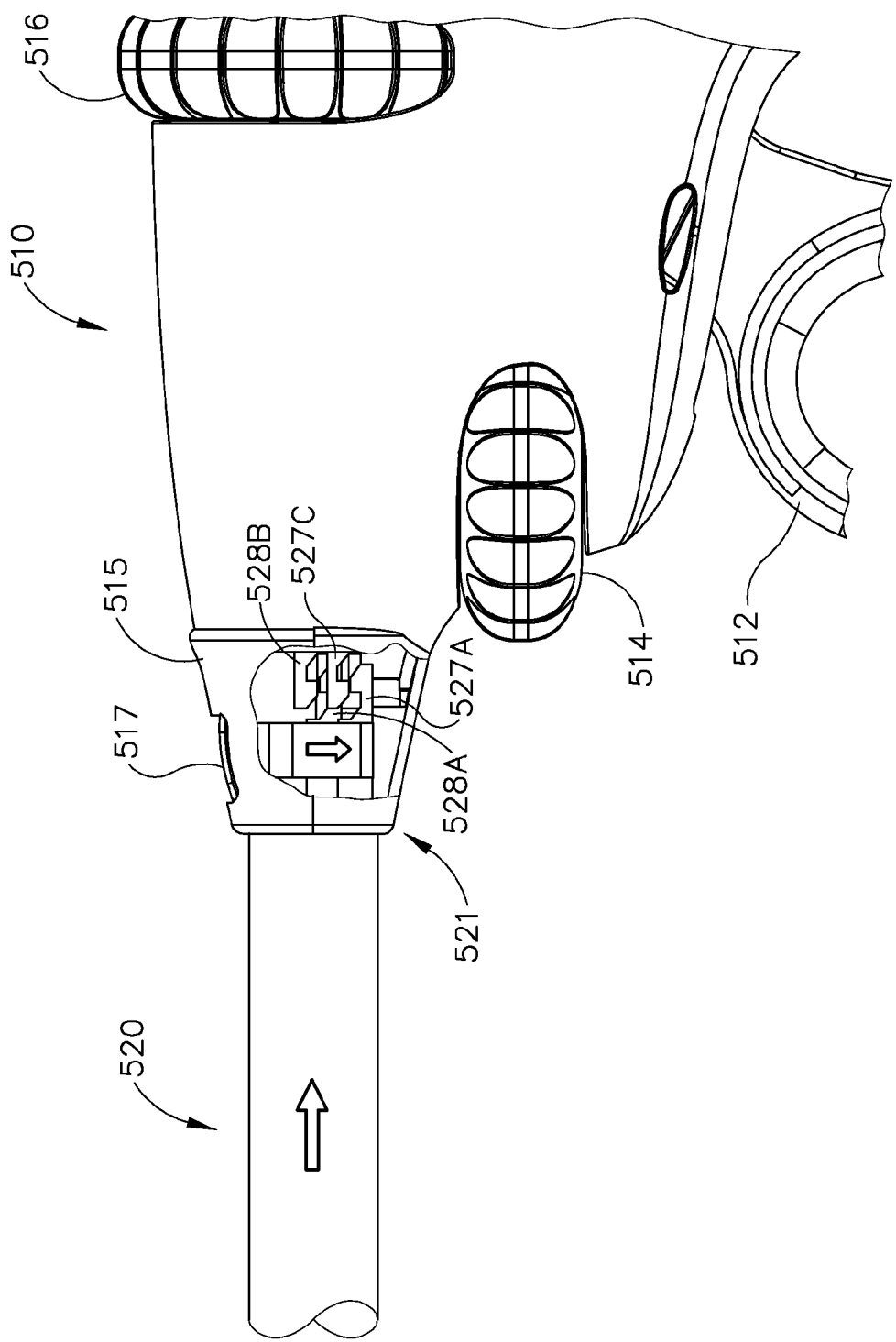
FIG. 39C depicts a partial side elevational view of the instrument of FIG. 28, with portions of the shaft and handle assemblies cut away to reveal internal components, with the shaft assembly at a second stage of insertion into the handle assembly.
Figure 39D:
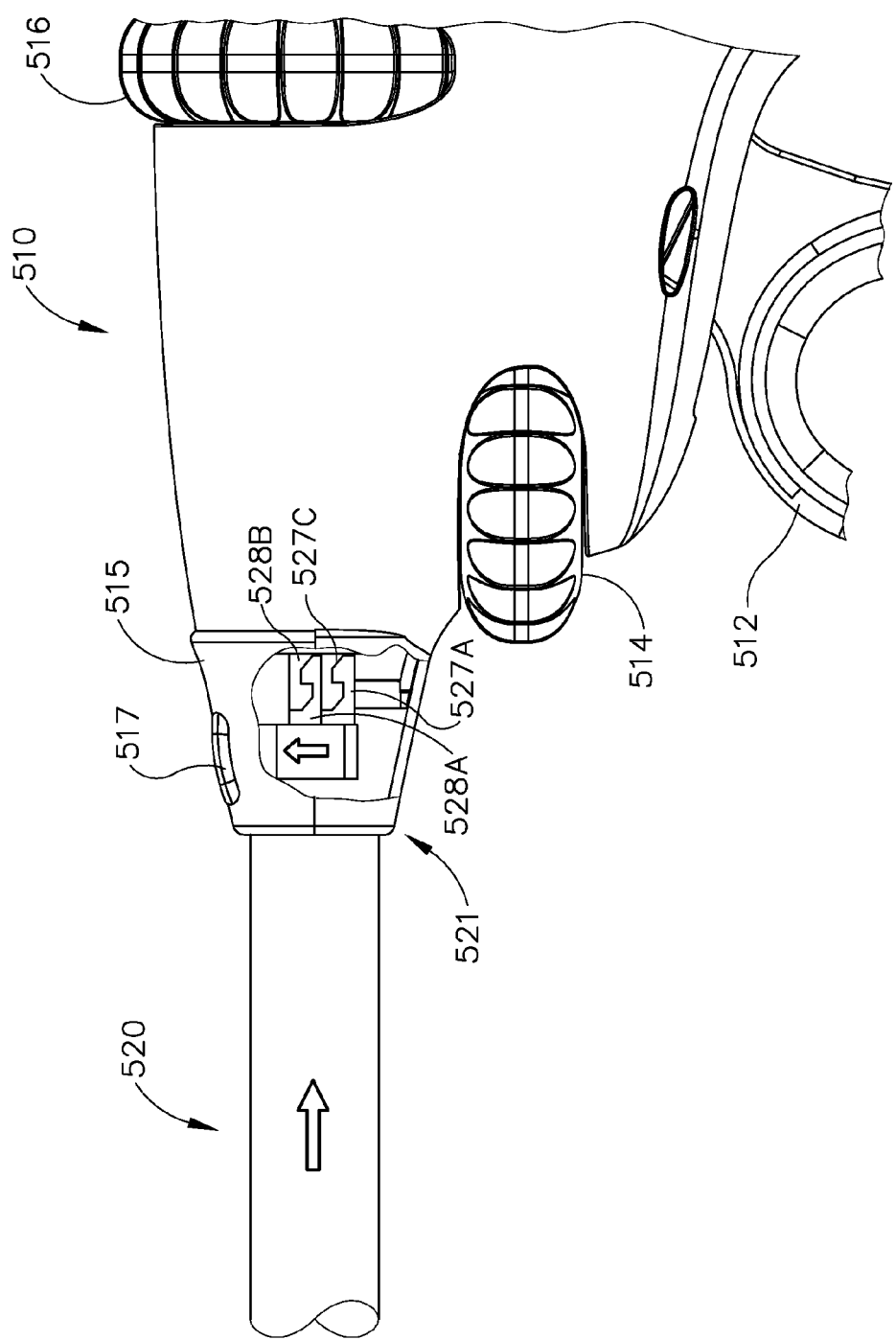
FIG. 39D depicts a partial side elevational view of the instrument of FIG. 28, with portions of the shaft and handle assemblies cut away to reveal internal components, with the shaft assembly fully coupled with the handle assembly.

FIGS. 39A-39D show an exemplary sequence of insertion of shaft (520) into handle assembly (510). In particular, FIG. 39A shows shaft (520) in a distal position. As shown in FIG. 39B, as shaft (520) is translated proximally into hub (515) of handle assembly (510), proximal ends (529A, 529B, 529C) of rods (527A, 527B, 528A) pass through openings (519) formed in button (517). In addition, angled surfaces (553A, 553B, 553C) of rods (527A, 527B, 528A) engage angled surfaces (554A, 554B, 554C) of rods (527C, 527D, 528B). As shown in FIG. 39C, as shaft (520) is translated further proximally, engagement between angled surfaces (553A, 553B, 553C) of rods (527A, 527B, 528A) and angled surfaces (554A, 554B, 554C) of rods (527C, 527D, 528B) causes deflection of proximal ends (529A, 529B, 529C) of rods (527A, 527B, 528A) through a camming action. As rods (527A, 527B, 528A) deflect downwardly, button (517) is driven from the first position to the second position. As shown in FIG. 39D, as shaft (520) is translated further proximally, projections (550A, 550B, 550C) of rods (527C, 527D, 528B) align with slots (551A, 551B, 551C) of rods (527A, 527B, 528A) such that rods (527A, 527B, 528A) resiliently return to their original straight configuration as projections (550A, 550B, 550C) engage slots (551A, 551B, 551C). As rods (527A, 527B, 528A) return to their original straight configuration, button (517) is returned to the first position.

Figure 40A:
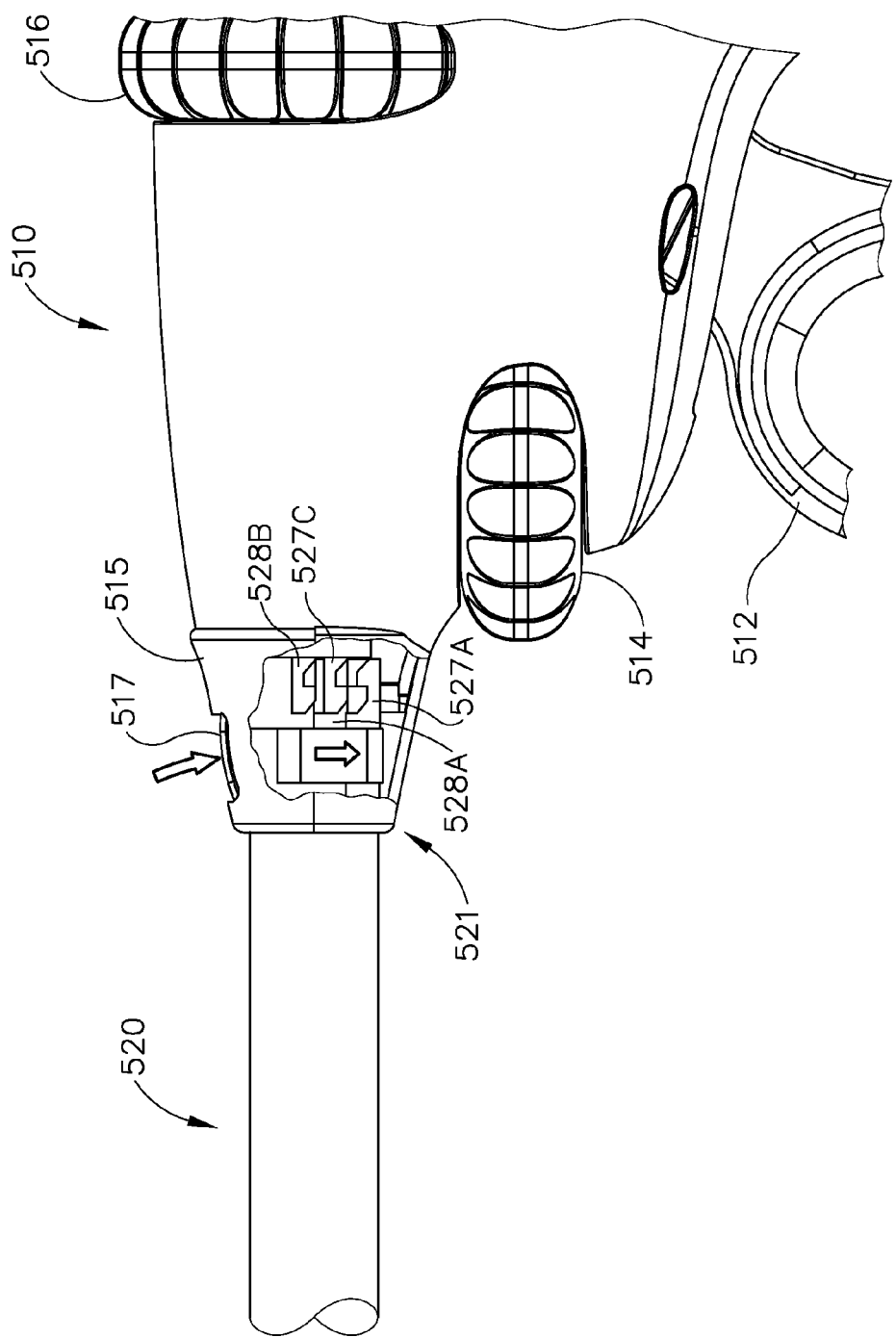
FIG. 40A depicts a partial side elevational view of the instrument of FIG. 28, with portions of the shaft and handle assemblies cut away to reveal internal components, with a button of the handle assembly depressed to initiate decoupling of the shaft assembly from the handle assembly.
Figure 40B:
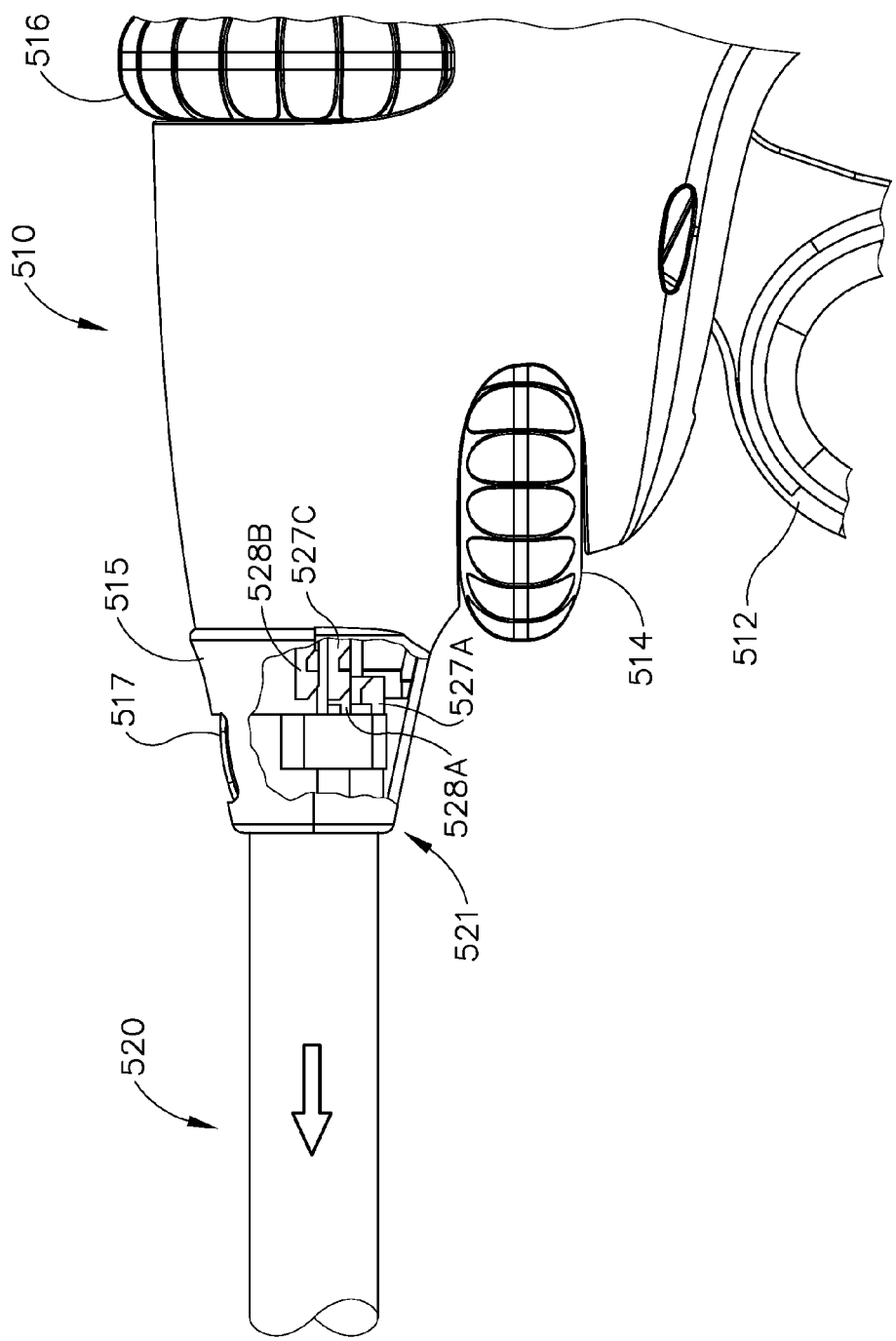
FIG. 40B depicts a partial side elevational view of the instrument of FIG. 28, with portions of the shaft and handle assemblies cut away to reveal internal components, with the shaft assembly being pulled distally away from the handle assembly to decouple the shaft assembly from the handle assembly.

To disengage shaft (520) from handle assembly (510), an operator drives button (517) toward the second position so as to cause deflection of proximal ends (529A, 529B, 529C) of rods (527A, 527B, 528A) as shown in FIG. 40A. As rods (527A, 527B, 528A) deflect downwardly, projections (550A, 550B, 550C) of rods (527C, 527D, 528B) disengage slots (551A, 551B, 551C) of rods (527A, 527B, 528A) such that shaft (520) may be removed from hub (515). Thus, while holding button (517) in the second position to disengage rods (527A, 527B, 528A) from rods (527A, 527B, 528A), the operator may pull shaft (520) distally to complete the removal of shaft (520) from handle assembly (510).

In some versions of instrument (500), shaft (520) and/or handle assembly (510) may be provided as being disposable or reusable. Versions with reusable components are intended to be cleaned, sterilized, and reused for multiple surgical procedures, and may include a flush port (not shown) to facilitate cleaning. In some such versions, the preferable life cycle of a reusable instrument may be at least 50 operations, more particularly at least 150 operations, or more particularly at least 200 operations. Reusable components may be built using materials that can withstand autoclave sterilization temperatures of at least 135 degrees Celsius, although low temperature materials can also be used with low temperature sterilization techniques known in the art.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body; (b) at least one user input feature; (c) an elongate shaft, wherein the elongate shaft comprises a distal end and a proximal end, wherein the elongate shaft extends distally from the body and defines a longitudinal axis; (d) a needle applier, wherein the needle applier is located at the distal end of the elongate shaft, wherein the needle applier further comprises: (i) a needle, and (ii) a drive assembly coupled to the needle, wherein the drive assembly is configured to drive the needle along an orbital path about a rotation axis that is transverse to the longitudinal axis, in response to an actuation of the user input feature; and (d) a motor, wherein the motor is configured provide motion to the needle applier to thereby actuate the drive assembly.

Example 2

The apparatus of Example 1, wherein the body comprises a transmission assembly, wherein the transmission assembly is configured to communicate motion from the motor to the needle applier to thereby actuate the drive assembly.

Example 3

The apparatus of Example 2, wherein the elongate shaft comprises an articulation joint, wherein the elongate shaft is operable to articulate at the articulation joint to thereby deflect the needle applier toward and away from the longitudinal axis of the elongate shaft.

Example 4

The apparatus of Example 3, wherein the motor is configured to provide motion to the articulation joint to thereby to drive articulation of the elongate shaft.

Example 5

The apparatus of Example 4, wherein the transmission assembly is configured to communicate motion from the motor to the articulation joint.

Example 6

The apparatus of Example 5, wherein the transmission assembly is configured to switch between communicating motion from the motor to the needle applier to thereby actuate the drive assembly and communicating motion from the motor to the articulation joint.

Example 7

The apparatus of Example 6, wherein the at least one user input feature comprises a first user input feature and a second user input feature.

Example 8

The apparatus of Example 7, wherein the first user input feature is operable cause communication of motion from the motor to the needle applier to thereby actuate the drive assembly, wherein the second user input feature is operable to cause communication of motion from the motor to the articulation joint.

Example 9

The apparatus of any one or more of Examples 2 through 8, wherein the distal end of the elongate shaft is rotatable about the longitudinal axis relative to the elongate shaft so as to cause rotation of the needle applier about the longitudinal axis relative to the elongate shaft.

Example 10

The apparatus of Example 9, wherein the motor is configured to provide rotary motion to the distal end of the elongate shaft to thereby drive rotation of the needle applier about the longitudinal axis of the elongate shaft.

Example 11

The apparatus of Example 10, wherein the transmission assembly is configured to communicate rotary motion from the motor to the distal end of the elongate shaft to thereby drive rotation of the needle applier about the longitudinal axis of the elongate shaft.

Example 12

The apparatus of Example 11, wherein the transmission assembly is configured to switch between communicating motion from the motor to the needle applier to thereby actuate the drive assembly and communicating motion from the motor to the distal end of the elongate shaft to thereby drive rotation of the needle applier about the longitudinal axis of the elongate shaft.

Example 13

The apparatus of Example 12, wherein the at least one user input feature comprises a first user input feature and a second user input feature.

Example 14

The apparatus of Example 13, wherein the first user input feature is operable cause communication of motion from the motor to the needle applier to thereby actuate the drive assembly, wherein the second user input feature is operable to cause communication of motion from the motor to the distal end of the elongate shaft to thereby drive rotation of the needle applier about the longitudinal axis of the elongate shaft.

Example 15

The apparatus of any one or more of Examples 2 through 14, wherein the transmission assembly comprises a solenoid, wherein the solenoid is operable to shift the transmission assembly between at least two states.

Example 16

The apparatus of any one or more of Examples 1 through 15, wherein the elongate shaft comprises a cartridge receiving assembly, wherein the needle applier comprises a cartridge removably coupled with the cartridge receiving assembly.

Example 17

The apparatus of any one or more of Examples 1 through 16, wherein the body comprises a battery pack, wherein the battery pack is configured to provide power to the motor.

Example 18

The apparatus of Example 17, wherein the battery pack is removably coupleable with the body.

Example 19

A surgical instrument comprising: (a) a body; (b) at least one user input feature; (c) an elongate shaft, wherein the elongate shaft comprises a distal end and a proximal end, wherein the elongate shaft extends distally from the body and defines a longitudinal axis, wherein the elongate shaft comprises an articulation joint; (d) a needle applier, wherein the needle applier is located distal to the articulation joint, the needle applier comprising: (i) a needle, and (ii) a drive assembly coupled to the needle, wherein the drive assembly is configured to drive the needle in an orbital motion about a rotation axis that is transverse to the longitudinal axis, in response to an actuation of the user input feature, wherein the articulation joint is operable to deflect the needle applier toward and away from the longitudinal axis of the elongate shaft, wherein the needle applier is rotatable relative to the elongate shaft about the longitudinal axis; and (e) a motor, wherein the motor is configured provide motion to the needle applier to thereby actuate the drive assembly, wherein the motor is further configured to provide motion to the articulation joint to thereby deflect the needle applier toward and away from the longitudinal axis of the elongate shaft, wherein the motor is further configured to drive rotation of the needle applier about the longitudinal axis.

Example 20

A surgical instrument comprising: (a) a body; (b) at least one user input feature; (c) an elongate shaft, wherein the elongate shaft comprises a distal end and a proximal end, wherein the elongate shaft extends distally from the body and defines a longitudinal axis, wherein the elongate shaft comprises an articulation joint; (d) a needle applier, wherein the needle applier is located distal to the articulation joint, the needle applier comprising: (i) a needle, and (ii) a drive assembly coupled to the needle, wherein the drive assembly is configured to drive the needle in an orbital motion about a rotation axis that is transverse to the longitudinal axis, in response to an actuation of the user input feature, wherein the articulation joint is operable to deflect the needle applier toward and away from the longitudinal axis of the elongate shaft; (e) a motor; and (f) a transmission assembly, wherein the transmission assembly is configured to switch between communicating motion from the motor to the needle applier to thereby actuate the drive assembly and communicating motion from the motor to the articulation joint to thereby deflect the needle applier toward and away from the longitudinal axis of the elongate shaft.

Example 21

A surgical instrument comprising: (a) a body; (b) a first drive element having a distal portion located at a distal end of the body; (c) at least one user input feature operable to cause motion of the first drive element; (d) a shaft, wherein the shaft is configured to removably couple with the distal end of the body, wherein the shaft defines a longitudinal axis; (e) a second drive element having a proximal portion located at a proximal end of the shaft, wherein the proximal portion of the second drive element is configured to removably couple with the distal portion of first drive element such that the first and second drive elements are aligned along a common axis and such that the first drive element is configured to communicate motion to the second drive element; and (f) a needle applier, wherein the needle applier is associated with the distal end of the elongate shaft, wherein the needle applier comprises: (i) a needle, and (ii) a drive assembly coupled to the needle, wherein the drive assembly is configured to drive the needle along an orbital path about a rotation axis that is transverse to the longitudinal axis, in response to motion of the second drive element.

Example 22

The apparatus of Example 21, wherein the first drive element comprises a first drive rod, wherein the second drive element comprises a second drive rod.

Example 23

The apparatus of Example 22, wherein a distal end of the first drive rod is configured to removably couple with a proximal end of the second drive rod.

Example 24

The apparatus of Example 23, wherein the first and second drive rods comprise mating projections and slots.

Example 25

The apparatus of any one or more of Examples 21 through 24, wherein the first drive element is operable to translate to thereby cause concurrent translation of the second drive element.

Example 26

The apparatus of Example 25, wherein the first and second drive elements are longitudinally translatable to thereby actuate the drive assembly.

Example 27

The apparatus of any one or more of Examples 21 through 26, wherein the first drive element is operable to rotate to thereby cause concurrent rotation of the second drive element.

Example 28

The apparatus of Example 27, wherein the needle applier is configured to rotate about the longitudinal axis, wherein the first and second drive elements are rotatable to thereby rotate the needle applier about the longitudinal axis.

Example 29

The apparatus of Example 28, wherein the first and second drive elements are further longitudinally translatable to thereby actuate the drive assembly.

Example 30

The apparatus of any one or more of Examples 21 through 29, wherein body further comprises a button operable to decouple the second drive element from the first drive element.

Example 31

The apparatus of any one or more of Examples 21 through 30, wherein the elongate shaft comprises an articulation joint, wherein the articulation joint is operable to deflect the needle applier toward and away from the longitudinal axis of the elongate shaft.

Example 32

The apparatus of Example 31, further comprising: (a) a third drive element having a distal portion located at the distal end of the body; and (b) a fourth drive element having a proximal portion located at the proximal end of the shaft, wherein proximal portion of the fourth drive element is configured to removably couple with the distal portion of third drive element such that the third and fourth drive elements are aligned along a common axis and such that the third drive element is configured to communicate motion to the fourth drive element; wherein the articulation joint is configured to deflect the needle applier toward and away from the longitudinal axis of the elongate shaft in response to motion of the fourth drive element.

Example 33

The apparatus of Example 32, further comprising: (a) a fifth drive element having a distal portion located at the distal end of the body; and (b) a sixth drive element having a proximal portion located at the proximal end of the shaft, wherein proximal portion of the sixth drive element is configured to removably couple with the distal portion of fifth drive element such that the fifth and sixth drive elements are aligned along a common axis and such that the fifth drive element is configured to communicate motion to the sixth drive element; wherein the articulation joint is configured to deflect the needle applier toward and away from the longitudinal axis of the elongate shaft in response to opposing longitudinal motion of the fourth and sixth drive elements.

Example 34

The apparatus of Example 33, wherein the first drive element and second drive element are configured to extend along a first axis, wherein the third drive element and the fourth drive element are configured to extend along a second axis, wherein the fifth drive element and the sixth element are configured to extend along a third axis, wherein the first, second, and third axes are parallel to the longitudinal axis, wherein the first, second, and third axes are offset from the longitudinal axis.

Example 35

The apparatus of any one or more of Examples 21 through 34, wherein the proximal portion of the second drive element is resiliently biased to engage the distal portion of the first drive element.

Example 36

The surgical instrument according to Example 35, further comprising an actuator, wherein the actuator is operable to deflect the proximal portion of the second drive element away from the distal portion of the first drive element to thereby disengage the proximal portion of the second drive element away from the distal portion of the first drive element.

Example 37

The apparatus of Example 36, wherein the actuator comprises a button located at the distal end of the body, wherein the button is operable to deform the proximal portion of the second drive element to thereby deflect the proximal portion of the second drive element away from the distal portion of the first drive element.

Example 38

The apparatus of any one or more of Examples 35 through 37, wherein the distal portion of the first drive element and the proximal portion of the second drive element comprise complementary cam features, wherein the cam features are operable to deflect the proximal portion of the second drive element away from the distal portion of the first drive element in response to the proximal portion of the second drive element being urged against the distal portion of the first drive element along a path that is parallel to the longitudinal axis.

Example 39

A surgical instrument comprising: (a) a body, wherein the body comprises: (i) a drive rod section, and (ii) a pair of articulation rod sections; (b) an elongate shaft, wherein the elongate shaft is removably coupleable with the body, wherein the elongate shaft defines a longitudinal axis, wherein the elongate shaft comprises: (i) an articulation joint, (ii) a drive rod section, wherein the drive rod section of the elongate shaft is configured to removably couple with the drive rod section of the body, and (iii) a pair of articulation rod sections, wherein the drive rod sections of the elongate shaft are configured to removably couple with the articulation rod sections of the body; and (c) a needle applier, wherein the needle applier is associated with the distal end of the elongate shaft, wherein the needle applier further comprises: (i) a needle, and (ii) a drive assembly coupled to the needle, wherein the drive assembly is configured to drive the needle along an orbital path about a rotation axis that is transverse to the longitudinal axis, wherein the elongate shaft is operable to articulate at the articulation joint to thereby deflect the needle applier toward and away from the longitudinal axis of the elongate shaft.

Example 40

A surgical instrument comprising: (a) a body; (b) a first drive element having a distal portion located at a distal end of the body; (c) at least one user input feature operable to cause motion of the first drive element; (d) a shaft, wherein the shaft assembly is configured to removably couple with the distal end of the body, wherein the shaft defines a longitudinal axis; (e) a second drive element having a proximal portion located at a proximal end of the shaft assembly, wherein the proximal portion of the second drive element is configured to removably couple with the distal portion of first drive element such that the first and second drive elements are aligned along a common axis and such that the first drive element is configured to communicate motion to the second drive element, wherein the proximal portion of the second drive element is resiliently biased to align with the common axis, wherein the first and second drive elements comprise complementary cam features, wherein the cam features are operable to deflect the proximal portion of the second drive element away from the distal portion of the first drive element in response to the proximal portion of the second drive element being urged against the distal portion of the first drive element along the common axis; and (f) a needle applier, wherein the needle applier is associated with the distal end of the elongate shaft, wherein the needle applier is configured to drive a needle along an orbital path about a rotation axis that is transverse to the longitudinal axis, in response to motion of the second drive element.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body;
   (b) a first drive element having a distal portion located at a distal end of the body;
   (c) at least one user input feature operable to cause motion of the first drive element;
   (d) an elongate shaft, wherein the elongate shaft is configured to removably couple with the distal end of the body, wherein the elongate shaft defines a longitudinal axis;
   (e) a second drive element having a proximal portion located at a proximal end of the elongate shaft, wherein the proximal portion of the second drive element is configured to removably couple with the distal portion of the first drive element such that the first and second drive elements are aligned along a common axis and such that the first drive element is configured to communicate motion to the second drive element, wherein the proximal portion of the second drive element is resiliently biased to engage the distal portion of the first drive element; and
   (f) a needle applier, wherein the needle applier is associated with the distal end of the elongate shaft, wherein the needle applier comprises:
      (i) a needle, and
      (ii) a drive assembly coupled to the needle, wherein the drive assembly is configured to drive the needle along an orbital path about a rotation axis that is transverse to the longitudinal axis, in response to motion of the second drive element.

2. The surgical instrument according to claim 1, wherein the first drive element comprises a first drive rod, wherein the second drive element comprises a second drive rod.

3. The surgical instrument according to claim 2, wherein a distal end of the first drive rod is configured to removably couple with a proximal end of the second drive rod.

4. The surgical instrument according to claim 3, wherein the first and second drive rods comprise mating projections and slots.

5. The surgical instrument according to claim 1, wherein the first drive element is operable to translate to thereby cause concurrent translation of the second drive element.

6. The surgical instrument according to claim 5, wherein the first and second drive elements are longitudinally translatable to thereby actuate the drive assembly.

7. The surgical instrument according to claim 1, wherein the first drive element is operable to rotate to thereby cause concurrent rotation of the second drive element.

8. The surgical instrument according to claim 7, wherein the needle applier is configured to rotate about the longitudinal axis, wherein the first and second drive elements are rotatable to thereby rotate the needle applier about the longitudinal axis.

9. The surgical instrument according to claim 8, wherein the first and second drive elements are further longitudinally translatable to thereby actuate the drive assembly.

10. The surgical instrument according to claim 1, wherein body further comprises a button operable to decouple the second drive element from the first drive element.

11. The surgical instrument according to claim 1, wherein the elongate shaft comprises an articulation joint, wherein the articulation joint is operable to deflect the needle applier toward and away from the longitudinal axis of the elongate shaft.

12. The surgical instrument according to claim 11, further comprising:
   (a) a third drive element having a distal portion located at the distal end of the body; and
   (b) a fourth drive element having a proximal portion located at the proximal end of the elongate shaft, wherein proximal portion of the fourth drive element is configured to removably couple with the distal portion of third drive element such that the third and fourth drive elements are aligned along a common axis and such that the third drive element is configured to communicate motion to the fourth drive element;
   wherein the articulation joint is configured to deflect the needle applier toward and away from the longitudinal axis of the elongate shaft in response to motion of the fourth drive element.

13. The surgical instrument according to claim 12, further comprising:
   (a) a fifth drive element having a distal portion located at the distal end of the body; and
   (b) a sixth drive element having a proximal portion located at the proximal end of the elongate shaft, wherein proximal portion of the sixth drive element is configured to removably couple with the distal portion of fifth drive element such that the fifth and sixth drive elements are aligned along a common axis and such that the fifth drive element is configured to communicate motion to the sixth drive element;

wherein the articulation joint is configured to deflect the needle applier toward and away from the longitudinal axis of the elongate shaft in response to opposing longitudinal motion of the fourth and sixth drive elements.

14. The surgical instrument according to claim 13, wherein the first drive element and second drive element are configured to extend along a first axis, wherein the third drive element and the fourth drive element are configured to extend along a second axis, wherein the fifth drive element and the sixth element are configured to extend along a third axis, wherein the first, second, and third axes are parallel to the longitudinal axis, wherein the first, second, and third axes are offset from the longitudinal axis.

15. The surgical instrument according to claim 1, further comprising an actuator, wherein the actuator is operable to deflect the proximal portion of the second drive element away from the distal portion of the first drive element to thereby disengage the proximal portion of the second drive element away from the distal portion of the first drive element.

16. The surgical instrument according to claim 15, wherein the actuator comprises a button located at the distal end of the body, wherein the button is operable to deform the proximal portion of the second drive element to thereby deflect the proximal portion of the second drive element away from the distal portion of the first drive element.

17. The surgical instrument according to claim 1, wherein the distal portion of the first drive element and the proximal portion of the second drive element comprise complementary cam features, wherein the cam features are operable to deflect the proximal portion of the second drive element away from the distal portion of the first drive element in response to the proximal portion of the second drive element being urged against the distal portion of the first drive element along a path that is parallel to the longitudinal axis.

18. A surgical instrument comprising:
(a) a body, wherein the body comprises:
 (i) a drive rod section, and
 (ii) a pair of articulation rod sections;
(b) an elongate shaft, wherein the elongate shaft is removably coupleable with the body, wherein the elongate shaft defines a longitudinal axis, wherein the elongate shaft comprises:
 (i) an articulation joint,
 (ii) a drive rod section, wherein the drive rod section of the elongate shaft is configured to removably couple with the drive rod section of the body, and
 (iii) a pair of articulation rod sections, wherein the articulation rod sections of the elongate shaft are configured to removably couple with the articulation rod sections of the body; and
(c) a needle applier, wherein the needle applier is associated with the distal end of the elongate shaft, wherein the needle applier further comprises:
 (i) a needle, and
 (ii) a drive assembly coupled to the needle, wherein the drive assembly is configured to drive the needle along an orbital path about a rotation axis that is transverse to the longitudinal axis,
wherein the drive rod sections of the body and the elongate shaft are longitudinally translatable to thereby actuate the drive assembly; and
wherein the elongate shaft is operable to articulate at the articulation joint to thereby deflect the needle applier toward and away from the longitudinal axis of the elongate shaft.

19. A surgical instrument comprising:
(a) a body;
(b) a first drive element having a distal portion located at a distal end of the body;
(c) at least one user input feature operable to cause motion of the first drive element;
(d) a shaft assembly, wherein the shaft assembly is configured to removably couple with the distal end of the body, wherein the shaft assembly defines a longitudinal axis;
(e) a second drive element having a proximal portion located at a proximal end of the shaft assembly, wherein the proximal portion of the second drive element is configured to removably couple with the distal portion of first drive element such that the first and second drive elements are aligned along a common axis and such that the first drive element is configured to communicate motion to the second drive element, wherein the proximal portion of the second drive element is resiliently biased to align with the common axis, wherein the first and second drive elements comprise complementary cam features, wherein the cam features are operable to deflect the proximal portion of the second drive element away from the distal portion of the first drive element in response to the proximal portion of the second drive element being urged against the distal portion of the first drive element along the common axis; and
(f) a needle applier, wherein the needle applier is associated with the distal end of the elongate shaft, wherein the needle applier is configured to drive a needle along an orbital path about a rotation axis that is transverse to the longitudinal axis, in response to motion of the second drive element.

* * * * *